(12) United States Patent
Huang et al.

(10) Patent No.: US 11,326,170 B2
(45) Date of Patent: May 10, 2022

(54) IMMUNOMODULATORY POLYNUCLEOTIDES AND USES THEREOF

(71) Applicant: CHANGCHUN HUAPU BIOTECHNOLOGY CO., LTD., Changchun (CN)

(72) Inventors: Tao Huang, Changchun (CN); Yan Shao, Changchun (CN); Jun Zhang, Changchun (CN)

(73) Assignee: Changchun Huapu Biotechnology Co. Ltd., Changchun (CN)

( * ) Notice: Subject to any disclaimer, the term of this patent is extended or adjusted under 35 U.S.C. 154(b) by 235 days.

(21) Appl. No.: 16/484,090

(22) PCT Filed: Apr. 17, 2018

(86) PCT No.: PCT/CN2018/083435
§ 371 (c)(1),
(2) Date: Aug. 6, 2019

(87) PCT Pub. No.: WO2018/192505
PCT Pub. Date: Oct. 25, 2018

(65) Prior Publication Data
US 2020/0002704 A1    Jan. 2, 2020

(30) Foreign Application Priority Data

Apr. 18, 2017 (CN) .......................... 201710251198.4

(51) Int. Cl.
| | |
|---|---|
| *C07H 21/02* | (2006.01) |
| *A61K 48/00* | (2006.01) |
| *C12N 15/117* | (2010.01) |
| *A61P 35/00* | (2006.01) |
| *C07K 14/57* | (2006.01) |
| *C12N 15/11* | (2006.01) |
| *A61K 45/06* | (2006.01) |
| *A61K 31/7115* | (2006.01) |

(52) U.S. Cl.
CPC ............ *C12N 15/117* (2013.01); *A61K 48/00* (2013.01); *A61P 35/00* (2018.01); *C07K 14/57* (2013.01); *C12N 15/111* (2013.01); *A61K 31/7115* (2013.01); *A61K 45/06* (2013.01)

(58) Field of Classification Search
CPC .................................................. C12N 15/113
See application file for complete search history.

(56) References Cited

U.S. PATENT DOCUMENTS

| | | |
|---|---|---|
| 5,229,275 A | 7/1993 | Goroff |
| 5,567,610 A | 10/1996 | Borrebaeck et al. |
| 5,571,894 A | 11/1996 | Wels et al. |
| 5,587,458 A | 12/1996 | King et al. |
| 5,658,738 A | 8/1997 | Nadeau et al. |
| 5,668,265 A | 9/1997 | Nadeau et al. |
| 5,869,046 A | 2/1999 | Presta et al. |
| 6,248,516 B1 | 6/2001 | Winter et al. |
| 7,488,802 B2 | 2/2009 | Collins et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,354,509 B2 | 1/2013 | Carven et al. |
| 8,513,390 B2 | 8/2013 | Stagliano et al. |
| 8,518,404 B2 | 8/2013 | Daugherty et al. |
| 8,552,154 B2 | 10/2013 | Freeman et al. |
| 8,779,108 B2 | 7/2014 | Queva et al. |
| 2008/0025980 A1 | 1/2008 | Hardy et al. |
| 2012/0149061 A1 | 6/2012 | Stagliano et al. |
| 2012/0237977 A1 | 9/2012 | Daugherty et al. |
| 2013/0022595 A1 | 1/2013 | Rotem-Yehudar et al. |
| 2013/0150558 A1 | 6/2013 | Williams et al. |
| 2014/0044738 A1 | 2/2014 | Langermann et al. |

FOREIGN PATENT DOCUMENTS

| | | |
|---|---|---|
| CN | 102719436 A | 10/2012 |
| CN | 104995213 A | 10/2015 |
| EP | 404097 A2 | 12/1990 |
| WO | 93/01161 A1 | 1/1993 |
| WO | 93/16185 A2 | 8/1993 |
| WO | 2004056875 A1 | 7/2004 |
| WO | 2007119815 A1 | 10/2007 |
| WO | 2008073959 A2 | 6/2008 |
| WO | 2011066389 A1 | 6/2011 |
| WO | 2013079174 A1 | 6/2013 |

OTHER PUBLICATIONS

Gao et al., Cancer Res, 73(24), 2013, 7211/7221).*
Ren et al. (Pathol. Oncol. Res., 2009, 15, 623-630).*
Bell D, et al. "In breast carcinoma tissue, immature dendritic cells reside within the tumor, whereas mature dendritic cells are located in peritumoral areas" Nov. 1999, Journal of Experimental Medicine, vol. 190, No. 10, pp. 1417-1426.
Chothia et al., "Canonical Structures for the Hypervariable Regions of Immunoglobulins" 1987, Journal of Molecular Biology, vol. 196, pp. 901-917.
Christian, S. et al. "Nucleolin expressed at the cell surface is a marker of endothelial cells in angiogenic blood vessels" Nov. 2003, Journal of Cell Biology, vol. 163, No. 4, pp. 871-878.
Crooke et al. "Progress in Antisense Oligonucleotide Therapeutics" Apr. 1996, Annual Review of Pharmacology and Toxicology, vol. 36, pp. 107-129.
Durand, M. et al., "Triple-helix formation by an oligonucleotide containing one (dA)12 and two (dT)12 sequences bridged by two hexaethylene glycol chains" 1992, Biochemistry, vol. 31, No. 38, pp. 9197-9204.

(Continued)

*Primary Examiner* — Amy H Bowman

(57) ABSTRACT

Provided are immunomodulatory polynucleotides with sequences of SEQ ID NOs:1-12 which are TLR9 agonists. Therapeutic combinations comprising the immunomodulatory polynucleotides are provided too.

37 Claims, 12 Drawing Sheets

Specification includes a Sequence Listing.

(56) References Cited

OTHER PUBLICATIONS

Fontanel, Marie Laurence et al., "Sterical recognition by T 4 polynucleotide kinase of non-nucleosidic moieties 51- attached to oligonucleotides" 1994, Nucleic Acids Research, vol. 22, No. 11, pp. 2022-2027.
Froehler, J. et al. "Triple-helix formation by oligodeoxynucleotides containing the carbocyclic analogs of thymidine and 5-methyl-2'-deoxycytidine" 1992, J. Am. Chem. Soc., vol. 114, No. 21, pp. 8320-8322.
Gabrilovich DI, et al. "Decreased antigen presentation by dendritic cells in patients with breast cancer" Mar. 1997, Clinical Cancer Research, vol. 3, pp. 483-490.
Gilliet M, et al. Plasmacytoid dendritic cells: sensing nucleic acids in viral infection and autoimmune diseases. Aug. 2008, Nat. Rev. Immunol.; vol. 8, No. 8, pp. 594-606.
Green et al, "Antigen-specific human monoclonal antibodies from mice engineered with human Ig heavy and light chain YACs" May 1994, Nature Genetics vol. 7, pp. 13-21.
Hartmann E., et al. "Identification and functional analysis of tumor-infiltrating plasmacytoid dendritic cells in head and neck cancer" Oct. 2003, Cancer Research, vol. 63, No. 19, pp. 6478-6487.
Heeley, R., et al. "Mutations Flanking the Polyglutamine Repeat in the Modulatory Domain of Rat Glucocorticoid Receptor Lead to an Increase in Affinity for Hormone" 2002, Endocrine Research, vol. 28, No. 3, pp. 217-229.
Hofmann MA, et al. "Phase 1 evaluation of intralesionally injected TLR9-agonist PF-3512676 in patients with basal cell carcinoma or metastatic melanoma" Jun. 2008, Journal of Immunotherapy, vol. 31, No. 5, pp. 520-527.
Hollinger et al., ""Diabodies": small bivalent and bispecific antibody fragments" Jul. 1993, Proc Natl Acad Sci USA, vol. 90, No. 14, pp. 6444-6448.
Hudson et al., "Engineered antibodies" Jan. 2003, Nature Medicine, vol. 9, No. 1, pp. 129-134.
Hunziker J. et al. "Nucleic Acid Analogues: Synthesis and Properties" 1995, Modern Synthetic Methods vol. 7, pp. 335-417.
ISA, International Search Report and Written Opinion for International Patent Application No. PCT/CN2018/083435 with English translation. 14 pages.
Jiang et al., "Pseudo-cyclic oligonucleotides: in vitro and in vivo properties" 1999, Bioorganic & Medicinal Chemistry, vol. 7, No. 12, pp. 2727-2735.
Johnson, K., et al. "Human Antibody Engineering" 1993, Current Opinion in Structural Biology, vol. 3, pp. 5564-5571.
Kindt et al., "Antibody Binding Site" 2007, Kuby Immunology, 6th ed., W.H. Freeman and Co., pp. 90-92.
Liljeblad et al., "Analysis of agalacto-IgG in rheumatoid arthritis using surface plasmon resonance" May 2000, Glycoconjugate Journal, vol. 17, No. 5, pp. 323-329.
Liu YJ. "IPC: professional type I interferon-producing cells and plasmacytoid dendritic cell precursors" 2005, Annu Rev Immunol. Vol. 23, pp. 275-306.
Lonberg, N. et al., "Antigen-specific human antibodies from mice comprising four distinct genetic modifications" Apr. 2004, Nature, vol. 368, pp. 856-859.
McCafferty et al., "Phage antibodies: filamentous phage displaying antibody variable domains" Dec. 1990, Nature, vol. 348, pp. 552-554.
Menetrier-Caux C, et al. "Inhibition of the differentiation of dendritic cells from CD34 (+) progenitors by tunor cells: role of interleukin-6 and macrophage colony-stimulating factor" 1998, Blood, vol. 92, pp. 4778-4791.
Nielson PE et al. "Peptide nucleic acid (PNA). A DNA mimic with a peptide backbone" 1994, Bioconjug Chem, vol. 5, No. 1, pp. 3-7.
Pluckthun, A., "Antibodies from *Escherichia Coli*" 1994, The Pharmacology of Monoclonal Antibodies, vol. 113, pp. 269-315.
Porkka et al., "A fragment of the HMGN2 protein homes to the nuclei of tumor cells and tumor endothelial cells in vivo." May 2002, Proc. Natl. Acad. Sci., USA, vol. 99, pp. 7444-7449.
Scott, A.M., et al. "Antibody therapy of cancer" Mar. 2012, Nature Reviews Cancer, vol. 12, No. 4, pp. 278-287.
Seliger, H. et al. "Oligonucleotide analogs with terminal 3'-3'- and 5'-5'-internucleotidic linkages as antisense inhibitors of viral gene expression" 1991, Nucleosides & Nucleotides, vol. 10, Nos. 1-3, pp. 469-477.
Stirchak EP et al. "Uncharged stereoregular nucleic acid analogs: 2. Morpholino nucleoside oligomers with carbamate internucleoside linkages" 1989, Nucleic Acids Research, vol. 17, No. 15, pp. 6129-6141.
Tarkoy, M. et al. Nucleic-Acid Analogues with Constraint Conformational Flexibility in the Sugar-Phasphate Backbone ('Bicyclo-DNA') Helvetica Chimica Acta, 1993, vol. 76, pp. 481-510.
Taylor, L. et al. "Human immunoglobulin transgenes undergo rearrangement, somatic mutation and class switching in mice that lack endogenous IgM" 1994, International Immunology, vol. 6, No. 4, pp. 579-591.
Tomoki I., et al. "Specialization, kinetics, and repertoire of type 1 interferon responses by human plasmacytoid predendritic cells" Mar. 2006, Blood, vol. 107, No. 6, pp. 2423-2431.
Treilleux I., et al. "Dendritic cell infiltration and prognosis of early stage breast cancer" Nov. 2004, Clinical Cancer Research, vol. 10, pp. 7466-7474.
Uhlmann E. et al. "Antisense Oligonucleotides: A New Therapeutic Principle" 1990, Chem Rev, vol. 90, pp. 544-584.
Uhlmann E, et al. "Chapter 16: Oligonucleotide Analogs Containing Dephospho-Internucleoside Linkages" 1993, Methods in Molecular Biology vol. 20: Protocols for Oligonucleotides and analogs, pp. 355-389.
Vandendriessche et al. "Acyclic oligonucleotides: possibilities and limitations" Aug. 1993 Tetrahedron, vol. 49, No. 33, pp. 7223-7238.
Wagner RW et al. "Potent and selective inhibition of gene expression by an antisense heptanucleotide" 1996, Nature Biotechnology, vol. 14, pp. 840-844.
Zou, W, et al. "Stromal-derived factor-I in human tumors recruits and alters the function of plasmacytoid precursor dendritic cells" Dec. 2001, Nature Medicine, vol. 7, pp. 1339-1346.

\* cited by examiner

A.

B.

C.

D.

A1.

B1.

A2.

B2.

A3.

B3.

A4.

B4.

A.

B.

C.

A.

B.

C.

A.

B.

C.

IMMUNOMODULATORY POLYNUCLEOTIDES AND USES THEREOF

CROSS REFERENCE TO RELATED APPLICATIONS

This application claims the benefit of, and priority to, Chinese Patent Application Serial No. 201710251198.4, filed on Apr. 18, 2017, the entire disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 6, 2019, is named SequenceListing.txt and is 4,096 bytes in size.

FIELD OF THE INVENTION

The present invention relates to compositions comprising immunomodulatory polynucleotides as therapeutics, such as for immunotherapy. Further, the present invention relates to the use of the compositions in the treatment of diseases such as cancers.

BACKGROUND OF THE INVENTION

Various TLR agonists have been investigated in clinical trials for their ability to promote antitumor immunity. The antitumor responses are largely attributed to their ability to stimulate APCs such as dendritic cells (DCs) which in turn, activate tumor-specific T cell responses.

Toll-like receptor 9 (TLR9) senses unmethylated CpG dinucleotides, a signature of microbial DNA, that can be mimicked by synthetic oligonucleotides containing CpG motifs (CpG ODNs). TLR9 stimulation by CpG DNA or CpG ODNs triggers intracellular signaling leading to the activation of macrophages, DCs and B cells, and the production of cytokines, chemokines, and immunoglobulins. Subsequently, cytokines produced by DC, such as IL-12, induce the differentiation of naive T cells into T helper 1 (Th1) and cytotoxic T-cells (CTL).

TLR9 agonists can elicit innate immune defenses and antigen T-cell specific responses, a property that underlines their development as vaccine adjuvants or immunotherapeutics for infectious diseases and cancer. Studies in animal models have demonstrated that the immune defenses mounted by CpG ODNs alone or as vaccine adjuvants can protect against a variety of viral, bacterial, and parasitic diseases. Promising results in the prophylactic treatment of hepatitis B have been obtained from phase III trials with a combination of a CpG ODN and hepatitis B surface antigen (Heplisav).

Antitumor activity of CpG ODNs has also been established in numerous mouse models. Encouraging results in the treatment of cancers have come from phase I and II clinical trials using CpG ODNs as a tumor vaccine adjuvant, monotherapy, or in combination with chemotherapy. However, there have been also some disappointing results with one pharmaceutical company recently dropping its clinical program with a TLR9 agonist in non-small cell lung cancer. The data of two phase 3 trials of PF-3512676 (formerly called CpG 2006) showed that it failed to improve the clinical outcomes compared to chemotherapy alone. There remains a need for continued identification of novel immunomodulatory polynucleotides.

Immunotherapies provide promising options for the treatment of diseases such as cancer and autoimmune diseases. The identification of a growing number of tumor-associated antigens (also termed tumor antigens herein) led to a broad collection of suitable targets for immunotherapy. On the other hand, Target-directed therapy, such as antibody-directed therapy, offers advantages over non-targeted therapy such as systemic therapy via oral or i.v. administration of drugs or whole-body therapy such as external radiation therapy (XRT). An advantage of antibody-directed therapy, and of therapy using monoclonal antibodies (MAbs) in particular, is the ability to deliver increased doses of a therapeutic agent to a tumor, with greater sparing of normal tissue from the effects of the therapeutic agent. This directed therapy might include the use of naked MAbs or MAbs conjugated to drugs, bacterial or other toxins, radionuclides, or neutron-capturing agents, such as boron addends.

In general, therapeutic antibodies kill tumor cells via three mechanisms (Scott A M, Wolchok J D, Old L J. Antibody therapy of cancer. Nat Rev Cancer. (2012), 12:278-87): (1) Direct antibody action, that is, blockade or agonist activity of ligand/receptor signaling, induction of apoptosis, and delivery of drugs or cytotoxic agents. Antibody receptor activation activity can produce direct tumor cell killing effect. For example, some antibodies can bind to receptors on the surface of tumor cells, activate the receptor, leading to apoptosis (e.g., in mitochondria). Antibodies can also mediate tumor cell killing by receptor-antagonistic activity. For example, certain antibodies can bind to cell surface receptors and block dimerization, kinase activation and downstream signaling, thereby inhibiting proliferation and promote apoptosis. Binding of antibodies to an enzyme can lead to neutralization, signal abrogation, and cell death. (2) Through immune-mediated cell killing mechanisms include complement-dependent cytotoxicity (CDC), antibody-dependent cell-mediated cytotoxicity (ADCC), T cell function regulation, etc. Immune-mediated killing of tumor cells can be accomplished through the following ways: induction of phagocytosis, complement activation, antibody-dependent cell-mediated cytotoxicity, genetically modified T cells being targeted to the tumor by single-chain variable fragment (scFv), through antibody-mediated antigenic cross presentation to dendritic cell to activate T cells, inhibition of T cell inhibitory receptors, such as cytotoxic T lymphocyte-associated antigen 4 (CTLA4). Of them, the Fc portion of the antibody feature is especially important for CDC and ADCC-mediated tumor cell killing effect. (3) Specific effect of antibody on tumor vasculature and matrix, through trapping of vascular receptor antagonist or ligand to induce vascular and stromal cells ablation, including: stromal cell inhibition, delivery of toxins to stromal cells, and delivery of toxins to the vasculature. (Scott A M, Wolchok J D, Old L J. Antibody therapy of cancer. Nat Rev Cancer. 2012, 12 (4):278-87).

Therapeutic monoclonal antibody drugs have advanced anti-cancer drug research and development. However, some issues still need further study to be solved, such as antibody immunogenicity, tolerance of long-term use of tumor target, and long-term effects of simple single blockade of signal transduction pathway. In short, a simple majority of antibodies are difficult to achieve long-term efficient inhibition and killing of tumor cells.

SUMMARY OF THE INVENTION

In one aspect, the present invention provided an immunomodulatory polynucleotide, comprising a sequence selected from the group consisting of: SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11 and SEQ ID NO.: 12.

In some embodiments, the polynucleotide comprises a chemical modification. In some embodiments, the polynucleotide comprises a modification of one or more phosphate groups. In some embodiments, the modification of one or more phosphate groups is a phosphorothioate linkage. In some embodiments, phosphate backbone of said polynucleotide is completely phosphorothioate-modified. In some embodiments, modification of one or more phosphate group is a linkage.

In another aspect, the present invention provides a method of modulating an immune response in a subject, comprising: administering to a subject an immunomodulatory polynucleotide provided herein, in an amount sufficient to modulate an immune response in said individual.

In another aspect, the present invention provides a method of increasing interferon-gamma (IFN-α) in a subject, comprising: administering an immunomodulatory polynucleotide provided herein to a subject in an amount sufficient to increase IFN-α in said subject.

In yet another aspect, the present invention provides a method of increasing interferon-gamma (IFN-γ) in a subject, comprising: administering an immunomodulatory polynucleotide provided herein to a subject in an amount sufficient to increase IFN-γ in said subject.

In a further aspect, the present invention provides a method of ameliorating a symptom of an infectious disease in a subject, comprising: administering an effective amount of an immunomodulatory polynucleotide provided herein to a subject, wherein an effective amount is an amount sufficient to ameliorate a symptom of said infectious disease.

In another aspect, the present invention provides a method of treating a cancer or tumor in a subject, comprising: administering an effective amount of an immunomodulatory polynucleotide provided herein to a subject, wherein an effective amount is an amount sufficient to treat said cancer or tumor.

In another aspect, the present invention provides a therapeutic combination, comprising: (i) an effective amount of a targeted therapeutic against a cancer; and (ii) an effective amount of an immunomodulatory polynucleotide provided herein, or a combination thereof.

In some embodiments, the targeted therapeutic is capable of binding to a tumor cell specifically or preferably in comparison to a non-tumor cell. In some embodiments, the tumor cell is of a carcinoma, a sarcoma, a lymphoma, a myeloma, or a central nervous system cancer. In some embodiments, the targeted therapeutic is capable of binding to a tumor antigen specifically or preferably in comparison to a non-tumor antigen.

In some embodiments, the tumor antigen is selected from the group consisting of: CD2, CD19, CD20, CD22, CD27, CD33, CD37, CD38, CD40, CD44, CD47, CD52, CD56, CD70, CD79, and CD137.

In some embodiments, the tumor antigen is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING (stimulator of IFN genes), Syndecan-1, TALI, TAG-72, Tenascin, TIM3, TRAILR1, TRAILR2, VEGFR-1, VEGFR-2, VEGFR-3, and variants thereof.

In some embodiments, the targeted therapeutic comprises an immunoglobulin, a protein, a peptide, a small molecule, a nanoparticle, or a nucleic acid. In some embodiments, the targeted therapeutic comprises an antibody, or a functional fragment thereof. In some embodiments, the antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Opdivo (nivolumab), Dacetuzumab, Urelumab, Tecentriq (atezolizumab, MPDL3280A), Lambrolizumab, Blinatumomab, CT-011, Keytruda (pembrolizumab, MK-3475), BMS-936559, MED14736, MSB0010718C, Imfinzi (durvalumab), Bavencio (avelumab) and margetuximab (MGAH22).

In some embodiments, the targeted therapeutic comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

In some embodiments, the targeted therapeutic comprises a ATWLPPR polypeptide of VEGFR, Thrombospondin-1 mimetics, CDCRGDCFCG (cyclic) polypeptide, SCH 221153 fragment, NCNGRC (cyclic) polypeptide, CTTHWGFTLC polypeptide, CGNKRTRGC polypeptide (LyP-1), Octreotide, Vapreotide, Lanreotide, C-3940 polypeptide, Decapeptyl, Lupron, Zoladex, or Cetrorelix.

In some embodiments, the targeted therapeutic comprises extracellular domains (ECD) or soluble form of PD-1, PDL-1, CTLA4, BTLA, KIR, TIM3, 4-1BB, LAG3, full length of partial of a surface ligand amphiregulin, betacellulini, EGF, ephrin, epigen, epiregulin, IGF, neuregulin, TGF, TRAIL, or VEGF.

In some embodiments, the combination provided herein further comprises a chemotherapeutic agent. In some embodiments, the chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

In a further aspect, the present invention provides a method for treating a disease condition in a subject that is in need of such treatment, comprising: administering to the subject a therapeutic combination provided herein. In some embodiments, the diseases condition is tumor.

In some embodiments, the disease condition comprises abnormal cell proliferation. In some embodiments, the abnormal cell proliferation comprises a pre-cancerous lesion. In some embodiments, the abnormal proliferation is of cancer cells. In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Tumor growth was analyzed using one-way ANOVA, survival data was analyzed using the Log-rank Mantel-Cox test. Differences were considered significant at a p value less than 0.05.

Figure 5:
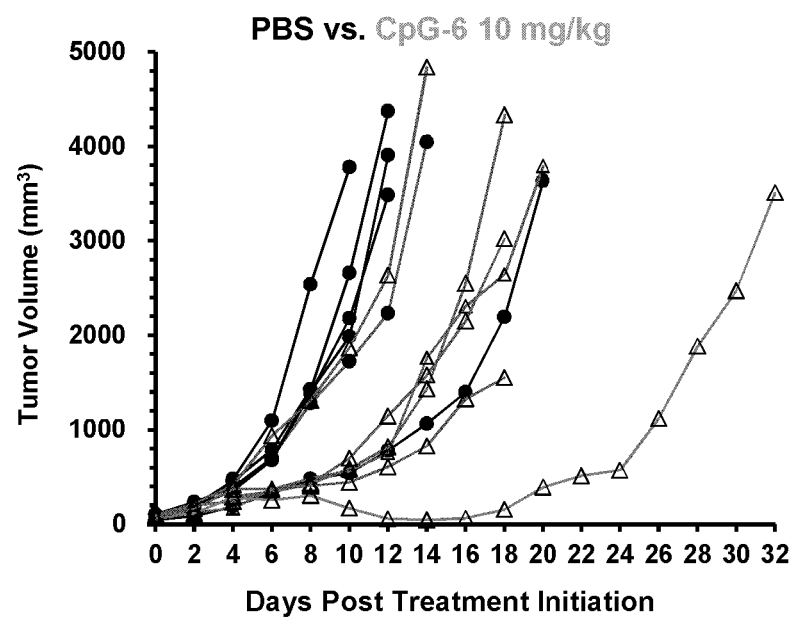
Figure 5:
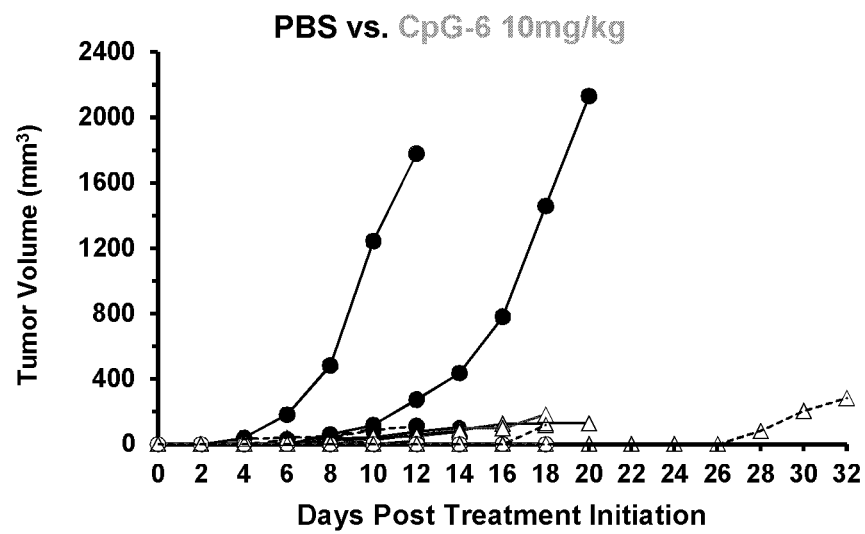
Figure 5:
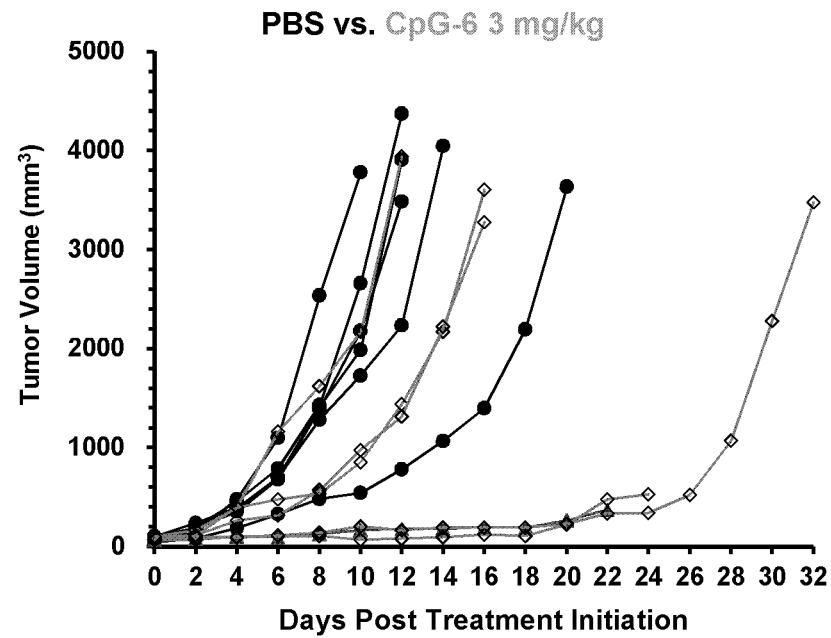
Figure 5:
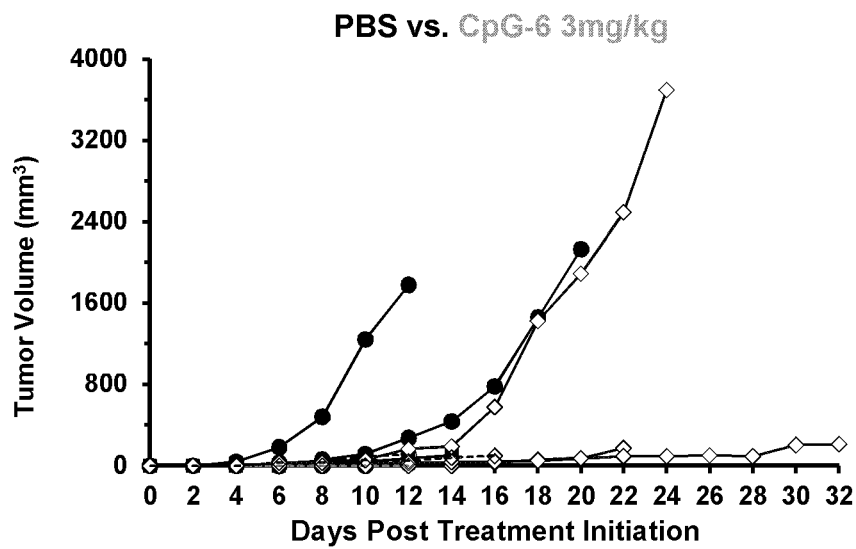
Figure 5:
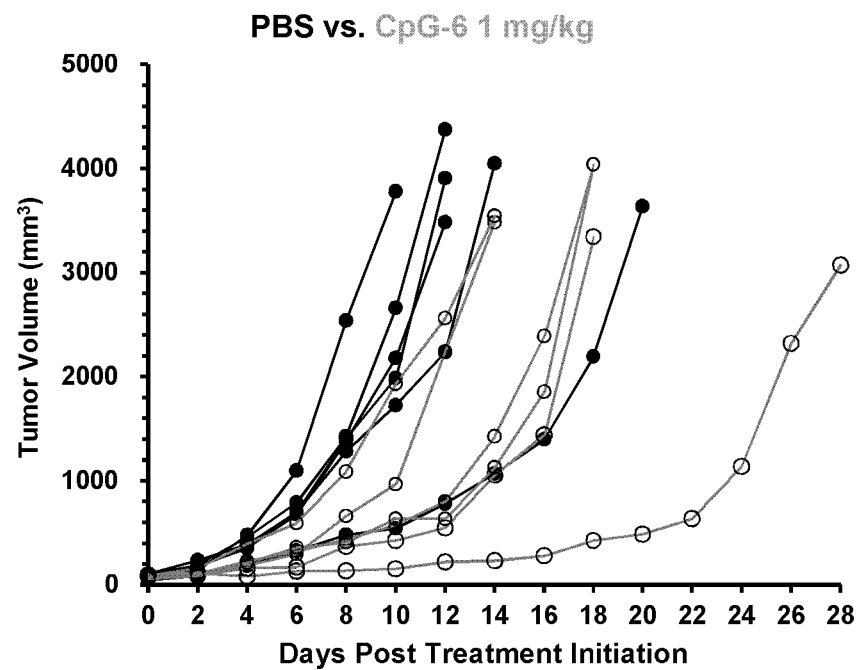
Figure 5:
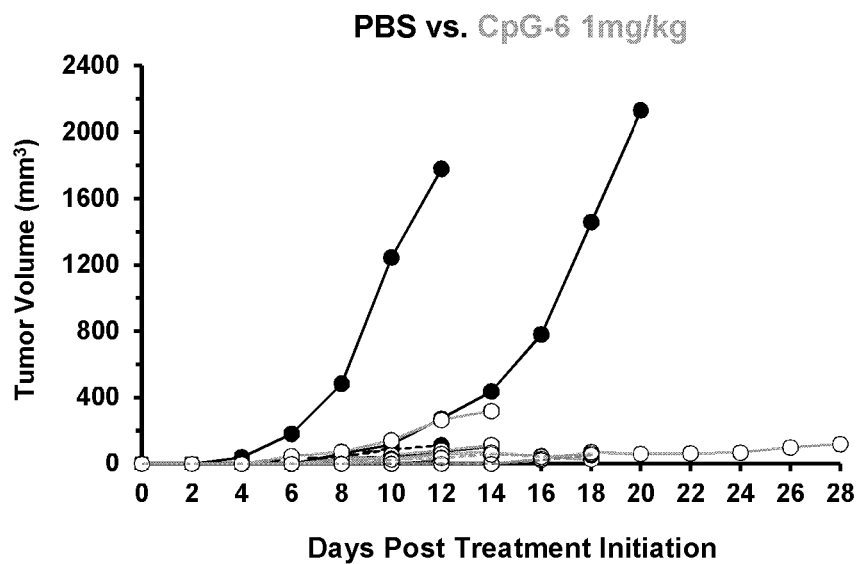
Figure 5:
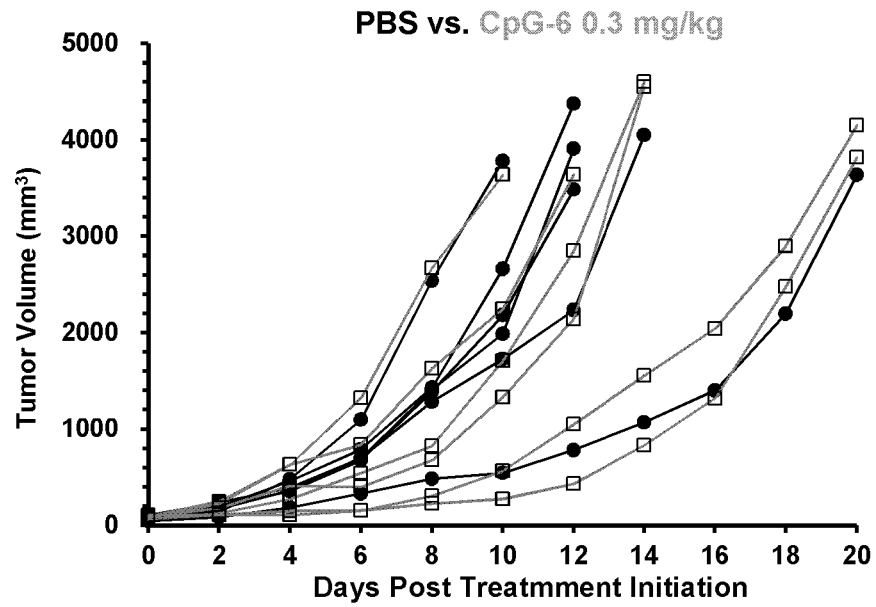
Figure 5:
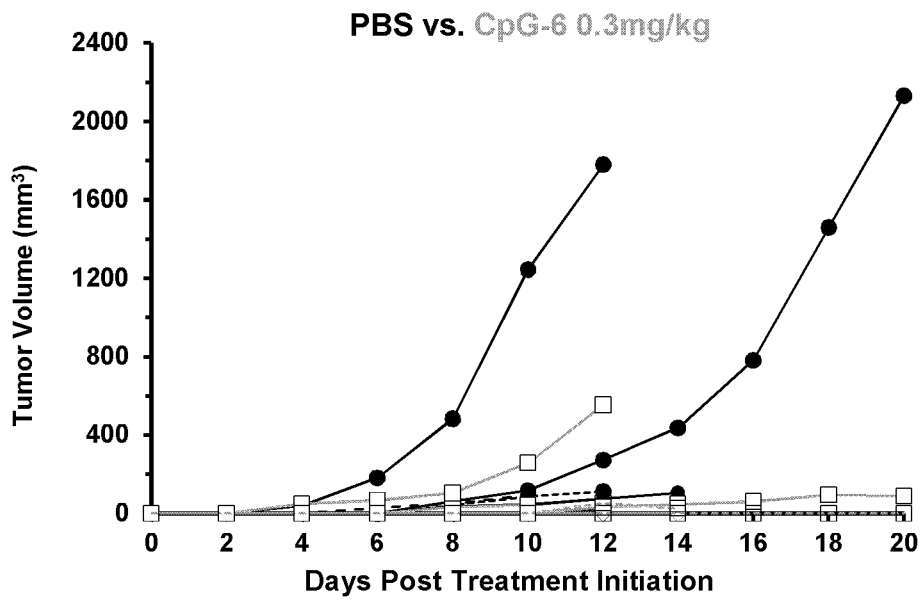
Figure 5:
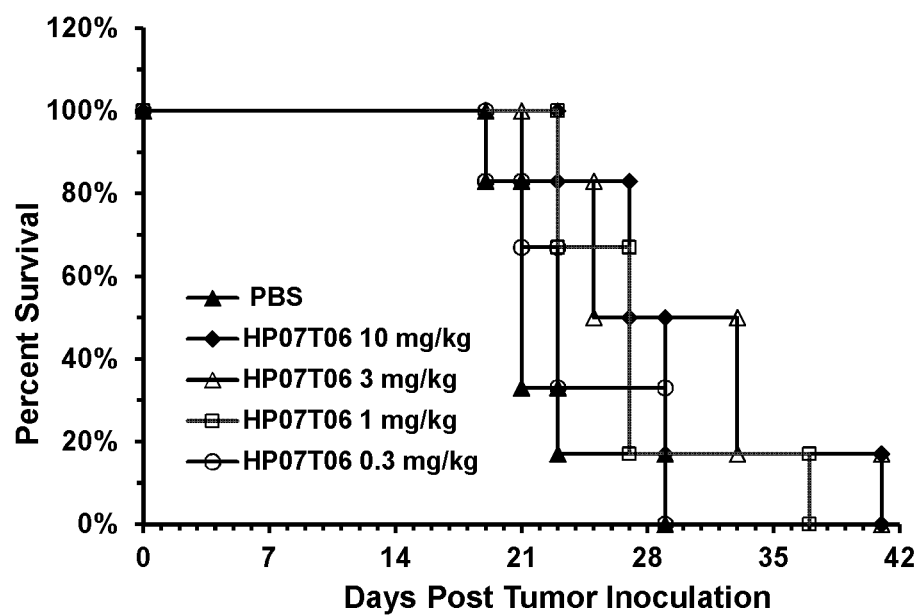

FIG. 5 depicts prolongation of survival of mice bearing B16F10 melanoma by Intratumoral CpG-6. C57BL/6 mice were inoculated s.c. on the right flank with $1\times10^5$ B16F10 cells on day 0, and on day 4 with $0.5\times10^5$ cells on the left frank. By day 9 when the right tumors reached approximately 85 mm³ in 5 groups (n=6), mice were randomly injected 0.3-10 mg/kg CpG-6 or PBS-vehicle into the right flank tumors, once/day on every other day for 5 doses. Animals were then followed for tumor growth on right (A1-A4) and left (B1-B4) flanks, in addition to survival (C). Statistical analysis of survival rates was performed using the Log-rank Mantel-Cox test in Prism (GraphPad) software v6. Differences were considered significant at a p value less than 0.05.

Figure 6:
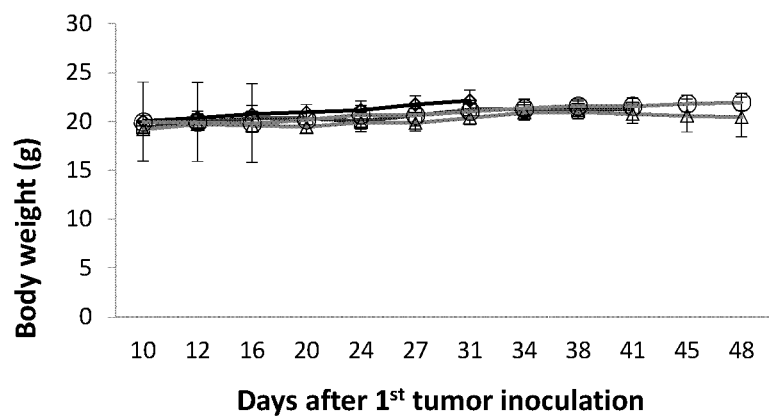
Figure 6:
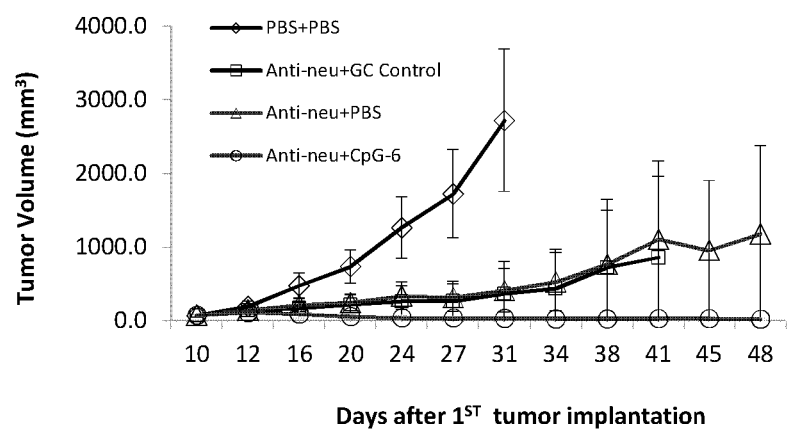
Figure 6:
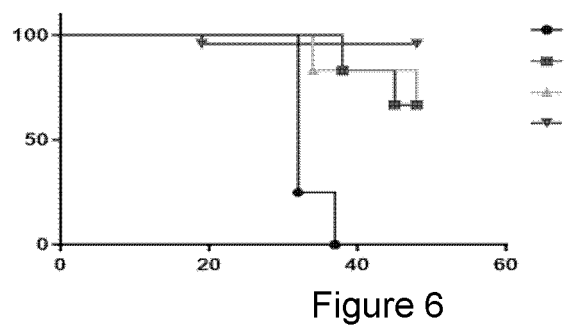

FIG. 6 depicts suppression of TUBO tumor growth by combinational treatment with intratumoral CpG-6 and systemic Anti-neu. BALB/c mice were inoculated s.c. with TUBO cells ($5\times10^5$/0.1 mL) on their upper right flank. By day 11 when tumors formed to approximately 60-120 mm³, mice were randomly grouped for combinational treatment. CpG-6, GC-control or PBS-vehicle was administrated i.t. once/day on every third day for 4 doses, while Anti-neu or PBS buffer injected i.v. once/week for 3 weeks. Each group consisted of 6 mice except CpG-6+Anti-neu (n=24). Mice were then followed for body weight change (A), tumor growth (B) and survival (C). All statistical analysis was performed using Prism (GraphPad) software v6. Tumor growth was analyzed using a repeated-measurement Two-Way ANOVA; survival data was analyzed using the Log-rank (Mantel-Cox) test and Gehan-Breslow-Wilcoxon test. Differences were considered significant at a p value <0.05.

Figure 7:
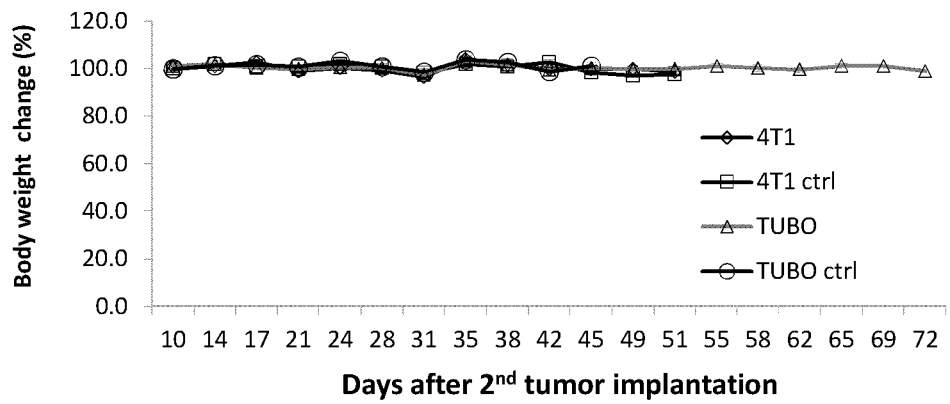
Figure 7:
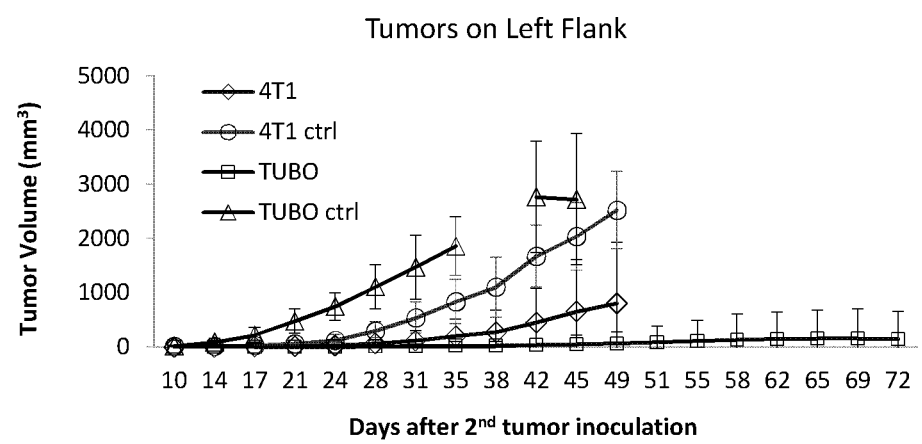
Figure 7:
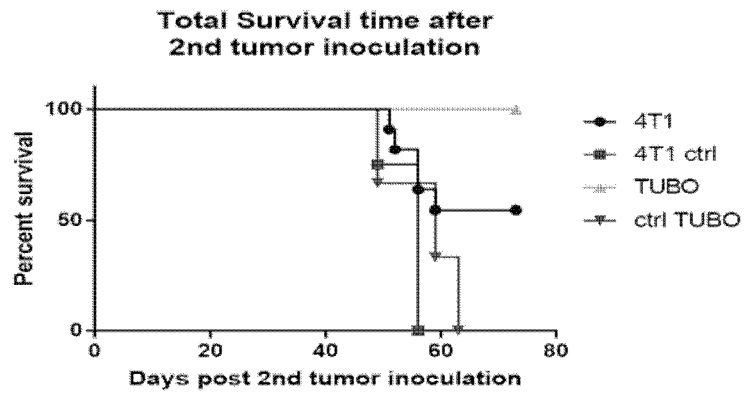

FIG. 7 depicts durable effect of CpG-6 and anti-neu joint treatment against TUBO tumor re-challenge. One month after the last dose of combinational treatment with Anti-neu and CpG-6, the survived mice were randomly divided into two groups (n=12) for a second s.c. inoculation of TUBO cells ($5\times10^5$/0.1 mL) or 4T1 cells ($1\times10^5$/0.1 mL) on their left flanks. Additional age and sex matched naïve mice (female 3-4 month old, 20-22 g) were employed as controls for tumor development after the first inoculation with the same amount of TUBO or 4T1 tumor cells. Mice were then followed for body weight change (A), tumor growth (B) and survival (C). All statistical analysis was performed using Prism (GraphPad) software v6. Differences were considered significant at a p value less than 0.05. Tumor growth was analyzed using unpaired Mann-Whitney t test, survival data was analyzed using the Log-rank Mantel-Cox test and Gehan-Breslow-Wilcoxon test.

Figure 8:
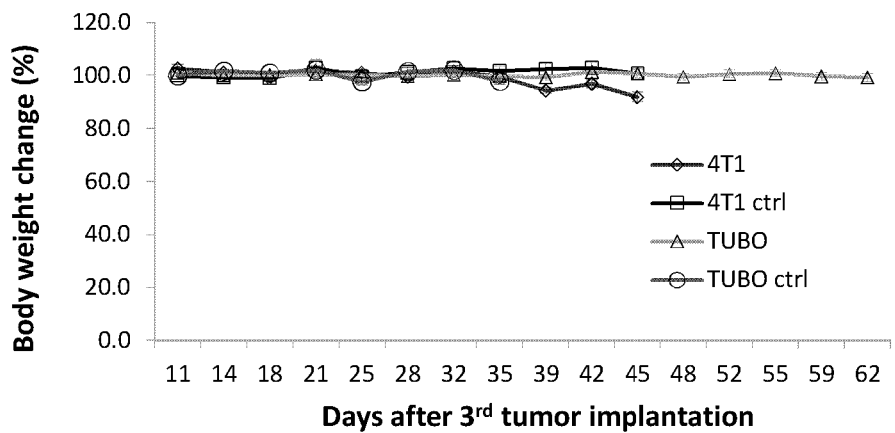
Figure 8:
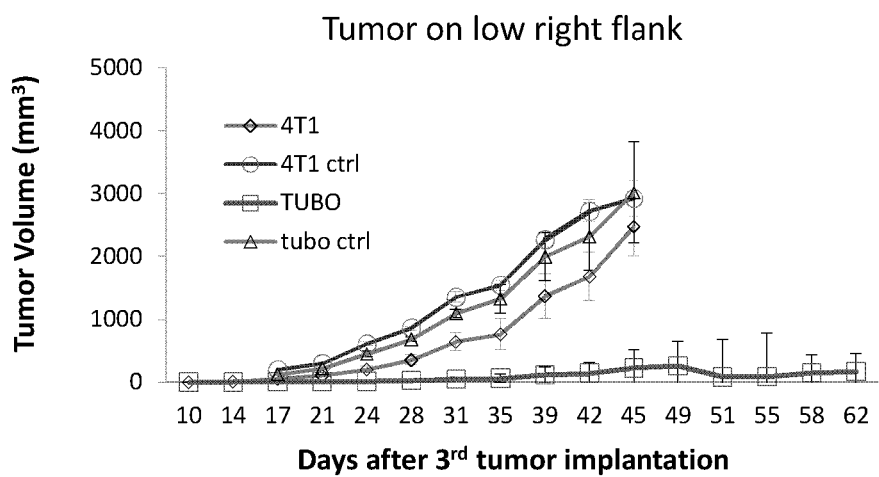
Figure 8:
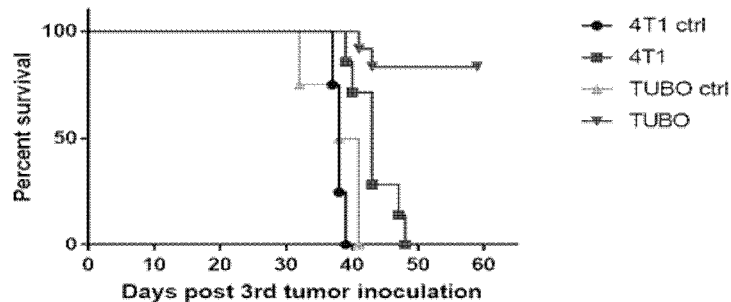

FIG. 8 depicts the long memory effect of CpG-6 and anti-neu combinational therapy against the 3rd TUBO implantation. One hundred days after the last dose of combinational treatment with Anti-neu and CpG-6, all survived mice in two sub-groups were inoculated s.c. on their lower right flanks with a third TUBO cells ($5\times10^5$/0.1 mL, n=12) or a second 4T1 cells ($1\times10^5$/0.1 mL, n=6) correspondingly. Once again a new set of naïve BALB/c mice (female, 6-7 month old, 24-35 g) were used as controls for tumor development following their first inoculation with the same amount of TUBO or 4T1 tumor cells. Mice were then followed for body weight change (A), tumor growth (B) and survival (C). All statistical analysis was performed using Prism (GraphPad) software v6. Differences were considered significant at a p value less than 0.05. Tumor growth was analyzed using a repeated-measurement Two-Way ANOVA, survival data was analyzed using the Log-rank Mantel-Cox test and Gehan-Breslow-Wilcoxon test.

DETAILED DESCRIPTION OF THE INVENTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

I. Definitions and Abbreviations

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well-known and commonly employed in the art. Standard techniques are used for nucleic acid and peptide synthesis. The techniques and procedures are generally performed according to conventional methods in the art and various general references, which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups, are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R"' and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$) akyl.

As used herein, the term "heteroatom" includes oxygen (O), nitrogen (N), sulfur (S), phosphorus (P) and silicon (Si).

II. The Compositions

In general, the present invention provides immunomodulatory polynucleotides, specifically synthetic oligonucleotides containing CpG motifs (CpG ODNs), and pharmaceutical compostions and combinations comprising the immunomodulatory polynucleotides, and methods for preventing or treating diseases (such as cancers) using such compositions.

A. TLR9 Agonists

In general, the composition of the present invention comprises a TLR9 agonist.

TLR9 is known to recognize unmethylated CpG motifs in bacterial DNA and in synthetic oligonucleotides. Other modifications of CpG-containing phosphorothioate oligonucleotides can also affect their ability to act as modulators of immune response through TLR9.

By "modulation" or "modulatory" herein is meant change, such as an increase in a response or qualitative difference in a TLR9-mediated response.

By "TLR9 agonist" herein is meant a compound, such as an oligonucleotide-based compound, that is able to enhance, induce, or modulate an immune stimulation mediated by TLR9.

In some embodiments, the TLR9 agonist comprises an immunomodulatory polynucleotide, such as an immunostimulatory polynucleotide.

By "immunostimulatory polynucleotide" herein is meant a nucleic acid molecule (e.g., polynucleotide) that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Immunostimulatory nucleic acid (ISNA) sequences are known to stimulate innate immune responses, in particular, those responses occur through TLR-9 signalling in the cell. As known in the art, immunostimulatory nucleic acid (ISNA) molecules can be isolated from microbial sources, such as bacteria, can be present in nucleic acid vectors for use in gene therapy, or can be synthesized using techniques and equipment described herein and known in the art. Generally, an immunostimulatory nucleic acid sequence include at least one CG dinucleotide, with the C of this dinucleotide being unmethylated. Accordingly, microbial infection and administered DNA can in some cases result in stimulation of innate immune responses.

By "immunostimulatory" or "stimulating an immune response" herein is meant stimulation of cell types that participate in immune reactions and enhancement of an immune response to a specific antigenic substance. An immune response that is stimulated by an immunostimulatory nucleic acid is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, 1L-2, IL-12, and TNF-β. Th2-type immune responses are generally associated with high levels of antibody production, especially IgE antibody production and enhanced eosinophils numbers and activation, as well as expression of Th2-associated cytokines such as IL-4, 1L-5 and IL-13.

By 'innate immune response" or "innate immunity" herein is meant to include a variety of innate resistance mechanisms by which a cell or individual recognizes and responds to the presence of a pathogen. As used herein, an "innate immune response" includes the intracellular and intercellular events and reactions that occur when the cell recognizes pathogen associated molecular patterns or signals. Cellular receptors active in an innate immune response include a family of Toll-like receptors (TLRs) and microbial ligands have been identified for several TLRs, as described herein. Examples of measurable innate immune responses include, but are not limited to, secretion of cytokines, activation or expansion of lymphocyte populations such as NK cells, CD4+ T lymphocytes, CD8+ T lymphocytes.

TLR9 agonist activates both innate and adaptive immune response (Arthur M. Krieg. Nature Reviews Drug Discovery, Vol 5. June 2006, 471-484). CpG containing oligonucleotides (CpG ODN) is a TLR9 agonist. D. M. Klinman, Nat. Rev., Immunol. 4 (2004) 249-258. Based on the functional characteristics, CpG ODNs are divided into three types. Tomoki Ito, et al. Blood, 2006, Vol 107, Num 6: 2423-2431. A-type CpG ODN activates human plasmacytoid dendritic cells (pDCs) to produce large amount of type I interferon (IFN-α/β) and strongly activates natural killer cells (NK cells). B-type CpG ODN primarily activates B cells, resulting in their proliferation and antibody secretion. C-type CpG ODN shares the activities of both A- and B-type CpG ODN. As a TLR9 agonist, CpG ODN such as CpG 2216 or CpG 2006 or CpG 2395 can be endocytosed into a cellular compartment where they are exposed to and activate TLR9. In pDC, TLR9 activation initiate a rapid innate immune response that is characterized by the secretion of pro-inflammatory cytokines (IL-6, tumor-necrosis factor-α (TNFα)), the secretion of type I interferon (IFN) and the secretion of secretion of IFN-inducible chemokines. Through both IFN-dependent and IFN-independent pathways, innate immune cells including natural killer (NK) cells, monocytes and neutrophils are secondarily activated by the pDC. B cells activated through TLR9 have a greatly increased sensitivity to antigen stimulation and efficiently differentiate into antibody-secreting cells, and therefore contributing to the adaptive immune response, especially humoral immune response. pDC activated through TLR9 secrete IFNα, which drives the migration and clustering of pDC to lymph nodes and other secondary lymphoid tissues where the pDC activates naive and memory T cells, assists the cross-presentation of soluble protein antigens to CD8+ cytotoxic T lymphocyte (CTL) and promotes strong TH1 biased cellular CD4 and CD8 T-cell responses. Based on the above mentioned findings, it is obvious that the agents that antagonize the activity of CpG ODN can be used to treat or prevent the immune-mediated disorder by inhibiting both innate and adaptive immune response.

In general, the TLR9 agonists of the present invention comprise an oligonucleotide (ODN).

By "Oligonucleotide" herein is meant means multiple nucleotides (i.e. molecules comprising a sugar (e.g. deoxyribose) linked to a phosphate group and to an exchangeable organic base, which is either a substituted pyrimidine (Py) (e.g., cytosine (C), thymine (T)) or a substituted purine (Pu) (e.g., adenine (A) or guanine (G)). The term oligonucleotide as used herein refers to oligodeoxyribonucleotide (ODN). The oligonucleotide can be obtained from existing nucleic acid sources (e.g., genomic or cDNA), but are preferably synthetic. The oligonucleotide of the invention can be synthesized by a variety of automated nucleic acid synthesizers available in the market. These oligonucleotides are referred to as synthetic oligonucleotides.

In some embodiments, the TLR9 agonist comprises an oligonucleotide that contains an unmethylated CpG motif.

In some embodiments, the TLR9 agonist comprising an oligonucleotide having a sequence selected from Table 1.

TABLE 1

TLR9 Agonists

| Name | Sequence |
| --- | --- |
| CpG 1 | 5'-tcgggaacgt tccccgcgtt cgaacgcgg-3' (SEQ ID No.: 1) |
| CpG 2 | 5'-tcgcgaacgt tcgcggcgtt cgaacgccg-3' (SEQ ID No.: 2) |
| CpG 3 | 5'-tcgcgaacgt tcgccgggtt cgaacccgg-3' (SEQ ID No.: 3) |
| CpG 4 | 5'-tcgcgaacgt tcgccgcctt cgaaggcgg-3' (SEQ ID No.: 4) |
| CpG 5 | 5'-tcgcgaacgt tcgccgcgat cgatcgcgg-3' (SEQ ID No.: 5) |
| CpG 6 | 5'-tcgcgaacgt tcgccgcgta cgtacgcgg-3' (SEQ ID No.: 6) |
| CpG 7 | 5'-tcgcgaacgt tcgccgcgcgt tcgaacgcgg-3' (SEQ ID No.: 7) |
| CpG 8 | 5'-tcgccgaacg ttcggccgcg gttcgaaccg cgg-3' (SEQ ID No.: 8) |
| CpG 9 | 5'-tcgcgaacgt tcgctcgcgt tcgaacgcgg-3' (SEQ ID No.: 9) |
| CpG 10 | 5'-tcgcgaacgt tcgccgacgt tcgaacgtcg g-3' (SEQ ID No.: 10) |
| CpG 11 | 5'-tcgcgaacgt tcgccggttc gaaccgg-3' (SEQ ID No.: 11) |
| CpG 12 | 5'-tcgcgaacgt tcgccgcttc gaagcgg-3' (SEQ ID No.: 12) |

In some embodiments, the oligonucleotides of the present invention comprise, or have, one of the sequences of Table 1, with one or additional nucleotides (such as 1, 2, 3, 4, o 5) at either 5' or 3' end, or both ends.

In some embodiments, the oligonucleotides of the present invention have exactly one of the sequences of Table 1, without any additional nucleotides at either the 5' end or the 3' end.

In some embodiments, the oligonucleotides of the present invention consist of one of the sequences of Table 1.

In some embodiments, the oligonucleotides of the present invention do not comprise a chemical modification. In some embodiments, the oligonucleotides of the present invention comprise a chemical modification.

The oligonucleotide disclosed in the invention can encompass various chemical modifications, in comparison to natural DNA, involving a phosphodiester internucleoside bridge, a ribose unit and/or a natural nucleoside base (adenine, guanine, cytosine, and thymine). The modifications can occur either during or after synthesis of the oligonucleotide. During the synthesis, modified bases can be incorporated internally or on its end. After the synthesis, the modification can be carried out using the active groups (via an amino modifier, via the 3' or 5' hydroxyl groups, or via the phosphate group).

An oligonucleotide according to the invention may have one or more modifications, wherein each modification is located at a particular phosphodiester internucleoside bridge and/or at a particular ribose unit and/or at a particular natural nucleoside base position in comparison to an oligonucleotide of the same sequence, which is composed of natural DNA. The chemical modification includes "back bone modification" of the oligonucleotide of the invention. As used herein, the modified back bone of the oligonucleotide of the invention includes, but not limited to the "phosphorothioate backbone" that refers to a stabilized sugar phosphate backbone of a nucleic acid molecule in which a non-bridging phosphate oxygen is replaced by sulfur at least one internucleotide linkage.

In some embodiments a non-bridging phosphate oxygen is replaced by sulfur at each and every internucleotide linkage. Other back bone modifications denote the modification with nonionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated.

In some embodiments, the phosphate backbone of the oligonucleotide is unmodified. In some embodiments phosphate backbone of the oligonucleotide is partially or completely phosphorothioate-modified. In some embodiments, the oligonucleotide is a phosphorothioate/phosphodiester chimera.

The chemical modification also includes the base substitutions of the oligonucleotide disclosed in the invention. The substituted purines and pyrimidines can be C-5 propyne pyrimidine and 7-deaza-7-substituted purine. The substituted purines and pyrimidines include but are not limited to adenine, cytosine, guanine, and thymine, and other naturally and non-naturally occurring nucleobases. The chemical modification of the oligonucleotide of the invention further includes the modification of the bases of the oligonucleotide. A modified base is any base which is chemically distinct from the naturally occurring bases typically found in DNA such as T, C, G and A, but which share basic chemical structures with these naturally occurring bases.

In some embodiments, the oligonucleotide of the invention is modified by using cytidine derivatives. The term "cytidine derivative" refers to a cytidine-like nucleotide (excluding cytidine) and the term "thymidine derivative" refers to a thymidine-like nucleotide (excluding thymidine). In addition, the oligonucleotides of the invention can be chemically modified by linking a diol, such as tetraethyleneglycol or hexaethyleneglycol, at either or both termini of the oligonucleotide.

The oligonucleotides may have further backbone modifications in addition to the phosphonoacetate or phosphonoacetate-like linkage at the Py-Pu dinucleotide. A stabilized internucleotide linkage is an internucleotide linkage that is relatively resistant to in vivo degradation (e.g., via an exo- or endo-nuclease), compared to a phosphodiester internucleotide linkage. In addition to the phosphonoacetate, and phosphonoacetate-like linkages, the oligonucleotides may contain other stabilized internucleotide linkages, including, without limitation, phosphorothioate, phosphorodithioate, methylphosphonate, and methylphosphorothioate. Other stabilized internucleotide linkages include, without limitation: peptide, alkyl, and dephospho. Phosphonoacetate internucleotide linkages, like other stabilized linkages, have reduced susceptibility to nuclease digestion and increased ability to activate RNAse H. Thus, for example phosphodiester, but not phosphonoacetate, oligonucleotides are susceptible to nuclease digestion, while both phosphodiester and phosphonoacetate oligonucleotides activate RNAse H. In some embodiments, the Py-Pu oligonucleotide includes at least one phosphodiester internucleotide linkage. The oligonucleotides may include, in addition to the phosphonoacetate or phosphonoacetate-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In one embodiment, the at least one phosphate modification of the backbone at each end is independently a phosphorothioate, phosphorodithioate, phosphonoacetate, phosphonoacetate-like, methylphosphonate, or methylphosphorothioate internucleotide linkage. In another embodiment, the degradation-resistant end includes one or more nucleotide units connected by peptide or amide linkages at the 3' end.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus, modified nucleic acids may include a 2'-O-alkylated deoxyribose group. In addition, modified nucleic acids may include sugars such as arabinose or 2'-fluoroarabinose instead of deoxyribose. Thus the nucleic acids may be heterogeneous in backbone composition thereby containing any possible combination of polymer units linked together such as peptide-nucleic acids (which have an amino acid backbone with nucleic acid bases). In the context of the instant invention, the oligonucleotides are not antisense oligonucleotides, ribozymes, or aptamers.

Nucleic acids also include substituted purines and pyrimidines such as C-5 propyne pyrimidine and 7-deaza-7-substituted purine modified bases (Wagner R W et al., (1996) Nat Biotechnol 14:840-4). Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The oligonucleotides may be DNA or RNA. In one embodiment the oligonucleotides of the invention are DNA/RNA hybrid molecules comprising a mixed backbone of ribose and deoxyribose. DNA/RNA hybrid oligonucleotides often demonstrate increased activities. In one embodiment these DNA/RNA hybrid oligonucleotides are single-stranded. In another embodiment all or part of the oligonucleotide is double-stranded. In one embodiment the oligonucleotides of the invention are in the form of covalently closed, dumbbell-shaped molecules with both primary and secondary structure. In one embodiment such cyclic oligoribonucleotides include two single-stranded loops connected by an intervening double-stranded segment. In one embodiment at least one single-stranded loop includes an immunostimulatory DNA motif of the invention. Other covalently closed, dumbbell-shaped molecules of the invention include chimeric DNA/RNA molecules in which, for example, the double-stranded segment is at least partially DNA (e.g., either homodimeric dsDNA or heterodimeric DNA:RNA) and at least one single-stranded loop includes an immunostimulatory DNA motif of the invention. Alternatively, the double stranded segment of the chimeric molecule is DNA.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann, E. et al., (1990) Chem Rev 90:543; "Protocols for Oligonucleotides and Analogs" Synthesis and Properties & Synthesis and Analytical Techniques, S. Agrawal, Ed, Humana Press, Totowa, USA 1993; Crooke, S T. et al., (1996) Annu Rev Pharmacol Toxicol 36:107-129; and Hunziker, J. et al., (1995) Mod Synth Methods 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from: a) the replacement of a phosphodiester internucleotide bridge located at the 3' and/or the 5' end of a nucleotide by a modified internucleotide bridge, b) the replacement of phosphodiester bridge located at the 3' and/or the 5' end of a nucleotide by a dephospho bridge, c) the replacement of a sugar phosphate unit from the sugar phosphate backbone by another unit, d) the replacement of a β-D-ribose unit by a modified sugar unit, and e) the replacement of a natural nucleotide base by a modified nucleotide base.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, NR1R2-phosphoramidate, boranophosphate, α-hydroxybenzyl phosphonate, phosphate-(C1-C21)-O-alkyl ester, phosphate-[(C6-C12)aryl-(C1-C21)-O-alkyl ester, d-alkylphosphonate and/or (C$_6$-C$_{12}$)arylphosphonate bridges, (C7-C12)-α-hydroxymethyl-aryl (e.g., disclosed in WO 95/01363), wherein (C6-C12)aryl, (C8-C20)aryl and (C6-C14)aryl are optionally substituted by halogen, alkyl, alkoxy, nitro, cyano, and where R1 and R2 are, independently of each other, hydrogen, (C1-C18)-alkyl, (C6-C20)-aryl, (C6-C14)-aryl-(C1-C8)-alkyl, preferably hydrogen, (C1-C8)-alkyl, preferably (C1-C4)-alkyl and/or methoxyethyl, or R1 and R2 form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology," Vol. 20, "Protocols for Oligonucleotides and Analogs," S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups. A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al., (1989) Nucleic Acids Res 17:6129-41), that is, e.g., the replacement by a morpholino-derivative unit; or to build up a polyamide nucleic acid ("PNA"; as described for example, in Nielsen P E et al., (1994) Bioconjug Chem 5:3-7), that is, e.g., the replacement by a PNA backbone unit, e.g., by 2-aminoethylglycine.

A β-D-ribose unit or a β-D-2'-deoxyribose unit can be replaced by a modified sugar unit, wherein the modified sugar unit is for example selected from α-D-2'-deoxyribose, α-L-2'-deoxyribose, β-L-2'-deoxyribose, β-L-ribose, 2'-F-21-deoxyribose, 2'-F-2'-deoxy-arabinose, 2'-O—(C1-C6)alkyl-ribose, preferably 2'-O—(C1-C6)alkyl-ribose is 2'-O-methylribose, 2I—O—(C2-C6)alkenyl-ribose, 21-[O—(C1-C6)alkyl-O—(C1-C6)alkyl]-ribose, 21-NH2-21-deoxyribose, β-D-xylo-furanose, α-arabinofuranose, 2,4-dideoxy-β-D-erythro-hexo-pyranose, and carbocyclic (described, for example, in Froehler, J. (1992) Am Chem Soc 114:8320) and/or open-chain sugar analogs (described, for example, in Vandendriessche et al., (1993) Tetrahedron 49:7223) and/or bicyclosugar analogs (described, for example, in Tarkov, M. et al., (1993) Helv Chim Acta 76:481).

In some embodiments the sugar is 2'-O-methylribose, 2'-deoxyribose, 2'-fluoro-2'-deoxyribose, 2'-amino-2'deoxyribose, 2'-O-alkyl-ribose, or 3'-O-alkyl-ribose and/or 2'-O-4'-C-alkylene ribose, such as 2'-O-4'-C-methylene ribose (also called LNA).

Nucleic acids also include substituted purines and pyrimidines such as C-5 propyne pyrimidine and 7-deaza-7-substituted purine modified bases (Wagner, R. W. et al., (1996) Nat Biotechnol 14:840-4). Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, 5-(C1-C6)-alkyluracil, 5-(C2-C8)-alkenyluracil, 5-(C2-C6)-alkynyluracil, 5-(hydroxymethyl)uracil, 5-chlorouracil, 5-fluorouracil, 5-bromouracil, 5-iodo-uracil, 2,4-difluoro-toluene, and 3-nitropyrrole, 5-hydroxycytosine, 5-(C1-C6)-alkylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

Herein "Py" is used to refer to pyrimidine and in some embodiments a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromocytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil). Some of the preferred cytosines include 5-methylcytosine, 5-fluorocytosine, 5-hydroxy-cytosine, 5-hydroxymethyl-cytosine, and N4-ethyl-cytosine. In another embodiment of the invention, the cytosine base is substituted by a universal base (e.g., 3-nitropyrrole, P-base), an aromatic ring system (e.g., fluorobenzene or difluorobenzene) or a hydrogen atom (dSpacer).

Herein "Pu" is used to refer to a purine or modified purine. In some embodiments Pu is a guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-hydroxyadenine) 8-substituted guanine (e.g., 8-hydroxyguanine and 8-bromoguanine), and 6-thioguanine. In another embodiment of the invention, the guanine base is substituted by a universal base (e.g., 4-methyl-indole, 5-nitro-indole, and K-base), an aromatic ring system (e.g., benzimidazole or dichloro-benzimidazole, 1-methyl-1H-[1,2,4]triazole-3-carboxylic acid amide) or a hydrogen atom (dSpacer).

The invention also encompasses oligonucleotides having unusual internucleotide linkages, including 5'-5', 2'-2', 2'-3', and 2'-5' internucleotide linkages. In some aspects of the invention it is advantageous for the oligonucleotides to have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'-3' linkage may be a phosphodiester, phosphorothioate, phosphonoacetate or any other modified internucleotide bridge. Methods for accomplishing such linkages are known in the art. For instance, such linkages have been described in Seliger, H. et al. Oligonucleotide analogs with terminal 3'-3'- and 5'-5'-internucleotidic linkages as antisense inhibitors of viral gene expression, Nucleotides & Nucleotides (1991), 10(1-3), 469-77 and Jiang et al., Pseudo-cyclic oligonucleotides: in vitro and in vivo properties, Bioorganic & Medicinal Chemistry (1999), 7(12), 2727-2735. In one embodiment such unusual linkages are excluded from the immunostimulatory DNA motif, even though one or more of such linkages may occur elsewhere within the polymer. For polymers having free ends, inclusion of one 3'-3' internucleotide linkage can result in a polymer having two free 5' ends. Conversely, for polymers having free ends, inclusion of one 5-5' internucleotide linkage can result in a polymer having two free 3' ends. Additionally, 3'3'-, 5-5'-, 2'-2'-, 2'-3'-, and 2'-5'-linked nucleic acids where the linkage is not a phosphodiester, phosphorothioate, phosphonoacetate or other modified bridge, can be prepared using an additional spacer, such as tri- or tetra-ethylenglycol phosphate moiety (Durand, M. et al., Triple-helix formation by an oligonucleotide containing one (dA)12 and two (dT)12 sequences bridged by two hexaethylene glycol chains, Biochemistry (1992), 31(38), 9197-204, U.S. Pat. Nos. 5,658,738, and 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 51-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

The oligonucleotide may contain a doubler or trebler unit (Glen Research, Sterling, Va.), in particular those modified oligodeoxyribonucleotide analogs with a 3'-3' linkage. A doubler unit in one embodiment can be based on 1,3-bis-[5-(4,4'-dimethoxytrityloxy)pentylamido]propyl-2-[(2-cyanoethyl)-(N,N-diisopropyl)]-phosphoramidite. A trebler unit in one embodiment can be based on incorporation of Tris-2,2,2-[3-(4,4'-dimethoxytrityloxy)propyloxymethyl]ethyl-[(2-cyanoethyl)-(N,N-diisopropyl)]-phosphoramidite.
Branching of the modified oligoribonucleotide analogs by multiple doubler, trebler, or other multiplier units leads to dendrimers which are a further embodiment of this invention. Branched modified oligoribonucleotide analogs may lead to crosslinking of receptors particularly for combinations of immunostimulatory RNA and DNA such as TLR3, TLR7, TLR8, and TLR9 with distinct immune effects compared to non-branched forms of the analogs. In addition, the synthesis of branched or otherwise multimeric analogs may stabilize DNA against degradation and may enable weak or partially effective DNA sequences to exert a therapeutically useful level of immune activity. The modified oligodeoxyribonucleotide analogs may also contain linker units resulting from peptide modifying reagents or oligonucleotide modifying reagents (Glen Research). Furthermore, the modified oligodeoxyribonucleotide analogs may contain one or more natural or unnatural amino acid residues which are connected to the polymer by peptide (amide) linkages.

The 3'-5', 5'-5', 3'-3\ 2'-2', 2'-3', and 2'-5' internucleotide linkages can be direct or indirect. Direct linkages in this context refers to a phosphate or modified phosphate linkage as disclosed herein, without an intervening linker moiety. An intervening linker moiety is an organic moiety distinct from a phosphate or modified phosphate linkage as disclosed herein, which can include, for example, polyethylene glycol, triethylene glycol, hexaethylene glycol, dSpacer (i.e., an abasic deoxynucleotide), doubler unit, or trebler unit. The linkages are preferably composed of C, H, N, O, S, B, P, and Halogen, containing 3 to 300 atoms. An example with 3 atoms is an acetal linkage (ODN1-3'-O—CH2-O-3'-ODN2) connecting e.g., the 3'-hydroxy group of one nucleotide to the 3'-hydroxy group of a second oligonucleotide. An example with about 300 atoms is PEG-40 (tetraconta polyethyleneglycol). Preferred linkages are phosphodiester, phosphorothioate, methylphosphonate, phosphoramidate, boranophosphonate, amide, ether, thioether, acetal, thioacetal, urea, thiourea, sulfonamide, Schiff Base and disulfide linkages. It is also possible to use the Solulink BioConjugation System.

If the oligonucleotide is composed of two or more sequence parts, these parts can be identical or different. Thus, in an oligonucleotide with a 3'3'-linkage, the sequences can be identical 5'-ODN1-3'3'-ODN1-5' or different 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides. Preferred are linked oligonucleotides which have two or more unlinked 5'-ends.

The oligonucleotide partial sequences may also be linked by non-nucleotidic linkers. A "non-nucleotidic linker" as used herein refers to any linker element that is not a nucleotide or polymer thereof (i.e., a polynucleotide), wherein a nucleotide includes a purine or pyrimidine nucleobase and a sugar phosphate, in particular abasic linkers (dSpacers), trietyhlene glycol units or hexaethylene glycol units. Further preferred linkers are alkylamino linkers, such as C3, C6, C12 aminolinkers, and also alkylthiol linkers, such as C3 or C6 thiol linkers. The oligonucleotides can also be linked by aromatic residues which may be further substituted by alkyl or substituted alkyl groups.

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In some embodiments, the activating moiety is capable of activating human immune cells, including but not limited to dendritic cells, and B cells, or a combination thereof.
Dendritic Cells In some embodiments, the ODNs provided herein is capable of activating dendritic cells, especially plasmacytoid dendritic cells.

Dendritic cells are the most powerful antigen-presenting cells. Dendritic cells play an essential role for the initiation of both innate and adaptive immune responses. Dendritic cells also play a key role in the induction and maintenance of immune tolerance.

By "dendritic cells" (DC) herein is meant a heterogeneous cell population including two main subtypes: namely, myeloid DC (mDC) and plasmacytoid DC (pDC) (Steinman et al., 1979, J. Exp. Med., 149, 1-16). These two blood DC subsets were originally differentiated by their expression of CD11c (integrin complement receptor) and CD123 (IL-3Rα). Each of the pDC and mDC populations constitutes between about 0.2 to about 0.6% of the PBMC population in humans.

By "pDC" herein is meant plasmacytoid dendritic cells and they represent a subtype of dendritic cells found in the blood and peripheral lymphoid organs. These cells express the surface markers CD123, BDCA-2(CD303) and BDCA-4(CD304) and HLA-DR, but do not express CD11c, CD14, CD3, CD20 or CD56, which distinguishes them from conventional dendritic cells, monocytes, T-cells, B cells and NK cells. As components of the innate immune system, these cells express intracellular Toll-like receptors 7 and 9, which enable the detection of viral and bacterial nucleic acids, such as ssRNA or CpG DNA motifs. Upon stimulation and subsequent activation, these cells produce large amounts of Type I interferon (mainly IFN-α and IFN-β) and Type III interferon (e.g., IFN-λ), which are critical pleiotropic antiviral compounds mediating a wide range of effects. By generating a large number of type I interferon, cytokines and chemokines, plasmacytoid dendritic cells are widely involved in the body's innate and adaptive immune responses. They can regulate NK cells, T cells, B cells and other cells involved in immune response intensity, duration, and response mode, thus play a very important function in tumor, infection and autoimmune disease. (Liu Y J. IPC: professional type 1 interferon-producing cells and plasmacytoid dendritic cell precursors. Annu Rev Immunol. 2005; 23:275-306. Gilliet M, Cao W, Liu Y J. Plasmacytoid dendritic cells: sensing nucleic acids in viral infection and autoimmune diseases. Nat Rev Immunol. 2008 August; 8 (8):594-606).

By "mDC" herein is meant myeloid dendritic cells and they represent a subtype of circulating dendritic cells found in blood and peripheral lymphoid organs. These cells express the surface markers CD11c, CD1a, HLA-DR and either BDCA-1 (CD1c) or BDCA-3 (CD141). They do not express BDCA-2 or CD123, which distinguishes them from pDC. mDC also do not express CD3, CD20 or CD56. As components of the innate immune system, mDC express Toll-like receptors (TLR), including TLR2, 3, 4, 5, 6 and 8, which enable the detection of bacterial and viral components. Upon stimulation and subsequent activation, these cells are the most potent antigen presenting cells to activate antigen-specific CD4 as well as CD8 T cells. In addition, mDCs has the ability to produce large amounts of IL-12 and IL23, which is critical for the induction of Th1-mediated or Th17 cell-mediated immunity.

Study found that many solid tumors such as breast cancer and head and neck cancer, ovarian cancer has pDC's invasion (Treilleux I, Blay J Y, Bendriss-Vermare N et al. Dendritic cell infiltration and prognosis of early stage breast cancer. Clin Cancer Res 2004; 10:7466-7474. Hartmann E, Wollenberg B, Rothenfusser S et al. Identification and functional analysis of tumor-infiltrating plasmacytoid dendritic cells in head and neck cancer. Cancer Res 2003; 63:6478-6487. Zou W P, Machelon V, Coulomb-L'Hermin A, et al. Stromal-derived factor-1 in human tumors recruits and alters the function of plasmacytoid precursor dendritic cells. Nat Med 2001; 7:1339-1346) and factors secreted by tumor cells inhibit DC maturation. (Gabrilovich D I, Corak J, Ciernik I F et al. Decreased antigen presentation by dendritic cells in patients with breast cancer. Clin Cancer Res 1997; 3:483-490. Bell D, Chomarat P, Broyles D et al. In breast carcinoma tissue, immature dendritic cells reside within the tumor, whereas mature dendritic cells are located in peritumoral areas. J Exp Med 1999; 190:1417-1425. Menetrier-Caux C, Montmain G, Dieu M C et al. Inhibition of the differentiation of dendritic cells from CD34 (+) progenitors by tumor cells: role of interleukin-6 and macrophage colony-stimulating factor. Blood 1998; 92:4778-4791). These immature DC cells did not play a role in promoting anti-tumor immunity. By contrast, DCs within the tumor microenvironment promote tumor growth by inhibiting antitumor immunity and by promoting angiogenesis. There is evidence that Toll-like receptor 9 agonist CpG drugs can stimulate pDC within the tumor microenvironment to inhibit tumor development. (Hofmann M A, Kors C, Audring H et al Phase 1 evaluation of intralesionally injected TLR9-agonist PF-3512676 in patients with basal cell carcinoma or metastatic melanoma. J Immunother 2008; 31:520-527).

In some embodiments, the human dendritic cell is a plasmacytoid dendritic cell.

B. Combination with Targeted Therapeutics

In another aspect, the present invention provides therapeutic combinations, or pharmaceutical compositions, comprising: (i) an effective amount of a targeted therapeutic against a cancer; (ii) an effective amount of immunomodulatory polynucleotides (e.g, a CpG ODN provided herein), or a combination thereof; and optionally (iii) one or more pharmaceutically acceptable carriers.

A therapeutic combination may be provided in a single pharmaceutical composition so that both the targeted therapeutics and the immunotherapeutic can be administered together. In alternative embodiments, a therapeutic combination may be provided using more than one pharmaceutical composition. In such embodiments, a targeted therapeutic may be provided in one pharmaceutical composition and an immunotherapeutic may be provided in a second pharmaceutical composition so that the two compounds can be administered separately such as, for example, at different times, by different routes of administration, and the like. Thus, it also may be possible to provide the targeted therapeutic and the immunotherapeutic in different dosing regimens.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

In general, the targeted therapeutics and the immunomodulatory polynucleotides are not linked to each other, such as by a covalent linker.

Targeted Therapeutics

In general, the combinations provided herein comprise a targeted therapeutic.

By "targeted therapeutic" herein is meant a therapeutic agent that binds specifically or selectively to a target molecule, cell, particle, tissue or aggregate, which generally is referred to as a "target" or a "marker," and these are discussed in further detail herein.

By "therapeutic agent" herein is meant an agent that has therapeutic effect, such as in ameliorating or treating cancers.

In some embodiments, the targeted therapeutic comprises an immunoglobulin, a protein, a peptide, a small molecule, a nanoparticle, or a nucleic acid.

In some embodiments, the targeted therapeutic comprises an antibody drug conjugate (ADC), as provided herein.

In some embodiments, the targeting therapeutic comprises an immunoglobulin, a protein, or a peptide, but does not contain a small molecule.

In some embodiments, the targeted therapeutic is not an ADC.

Exemplary targeted therapeutic such as antibodies (e.g., chimeric, humanized and human) are recognized in the art and are useful without limitation in practicing the present invention.

In some embodiments, a targeted therapeutic agent is an antibody, antibody fragment, bispecific antibody or other antibody-based molecule or compound.

In some embodiments, a targeted therapeutic agent is selected from aptamers, avimers, receptor-binding ligands, nucleic acids, biotin-avidin binding pairs, binding peptides or proteins, etc that both binds specifically or preferably to a target molecule and has therapeutic effect such as against cancers or tumors.

By "target" or "marker" herein is meant any entity that is capable of specifically binding to a particular targeted therapeutic, such as Her2/Neu. In some embodiments, targets are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1,000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

By "specifically binds" or "preferably binds" herein is meant that the binding between two binding partners (e.g., between a targeting moiety and its binding partner) is selective for the two binding partners and can be discriminated from unwanted or non-specific interactions. For example, the ability of an antigen-binding moiety to bind to a specific antigenic determinant can be measured either through an enzyme-linked immunosorbant assay (ELISA) or other techniques familiar to one of skill in the art, e.g. surface plasmon resonance technique (analyzed on a BIAcore instrument) (Liljeblad et al., Glyco J 17, 323-329 (2000)), and traditional binding assays (Heeley, Endocr Res 28, 217-229 (2002)). The terms "anti-[antigen] antibody" and "an antibody that binds to [antigen]" refer to an antibody that is capable of binding the respective antigen with sufficient affinity such that the antibody is useful as a diagnostic and/or therapeutic agent in targeting the antigen. In some embodiments, the extent of binding of an anti-[antigen] antibody to an unrelated protein is less than about 10% of the binding of the antibody to the antigen as measured, e.g., by a radioimmunoassay (RIA). In some embodiments, an antibody that binds to [antigen has a dissociation constant (KD) of <I µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). It is understood that the above definition is also applicable to antigen-binding moieties that bind to an antigen.

In certain specific embodiments, a target is a tumor marker. In some embodiments, a tumor marker is an antigen that is present in a tumor that is not present in normal organs, tissues, and/or cells. In some embodiments, a tumor marker is an antigen that is more prevalent in a tumor than in normal organs, tissues, and/or cells. In some embodiments, a tumor marker is an antigen that is more prevalent in malignant cancer cells than in normal cells.

By "tumor antigen" herein is meant an antigenic substance produced in tumor cells, i.e., it triggers an immune response in the host. Normal proteins in the body are not antigenic because of self-tolerance, a process in which self-reacting cytotoxic T lymphocytes (CTLs) and autoantibody-producing B lymphocytes are culled "centrally" in primary lymphatic tissue (BM) and "peripherally" in secondary lymphatic tissue (mostly thymus for T-cells and spleen/lymph nodes for B cells). Thus any protein that is not exposed to the immune system triggers an immune response. This may include normal proteins that are well sequestered from the immune system, proteins that are normally produced in extremely small quantities, proteins that are normally produced only in certain stages of development, or proteins whose structure is modified due to mutation.

In some embodiments, a target is preferentially expressed in tumor tissues and/or cells versus normal tissues and/or cells.

In some embodiments of the invention a marker is a tumor marker. The marker may be a polypeptide that is expressed at higher levels on dividing than on non-dividing cells. For example, Her-2/neu (also known as ErbB-2) is a member of the EGF receptor family and is expressed on the cell surface of tumors associated with breast cancer. Another example is a peptide known as F3 that is a suitable targeting agent for directing a nanoparticle to nucleolin (Porkka et al., 2002, Proc. Natl. Acad. Sci., USA, 99:7444; and Christian et al., 2003, J. Cell Biol., 163:871). It has been shown that targeted particles comprising a nanoparticle and the A10 aptamer (which specifically binds to PSMA) were able to specifically and effectively deliver docetaxel to prostate cancer tumors.

Antibodies or other drug that specifically target these tumor targets specifically interfere with and regulate signaling pathways of the biological behavior of tumor cells regulate directly, or block signaling pathway to inhibit tumor cell growth or induce apoptosis. To date, there are dozens of target drugs have been approved for solid tumors or hematological malignancies clinical research and treatment, and there are number of targeted drugs for hematological malignancies.

In some embodiments, the tumor antigen (or tumor target) is selected from the group consisting of: CD2, CD19, CD20, CD22, CD27, CD33, CD37, CD38, CD40, CD44, CD47, CD52, CD56, CD70, CD79, and CD137.

In some embodiments, the tumor antigen (or tumor target) is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y antigen, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING, Syndecan-1, TACI, TAG-72, Tenascin, TIM3, TRAILR1, TRAILR2, VEGFR-1, VEGFR-2, VEGFR-3, and variants thereof. The variants of the tumor antigen encompass various mutants or polymorphisms known in the art and/or naturally occurred.

In some embodiments, the targeted therapeutic comprises an antibody, or a functional fragment thereof.

By immunoglobulin" or "antibody" herein is meant a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter. Such antibodies include IgG1, IgG2a, IgG3, IgG4 (and IgG4 subforms), as well as IgA isotypes.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin The terms "full-length antibody", "intact antibody", and "whole antibody" are used herein interchangeably to refer to an antibody having a structure substantially similar to a native antibody structure or having heavy chains that contain an Fc region as defined herein.

By "native antibodies" herein is meant naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

By "antibody fragment" herein is meant a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), single-domain antibodies, and multispecific antibodies formed from antibody fragments. For a review of certain antibody fragments, see Hudson et al., Nat Med 9, 129-134 (2003). For a review of scFv fragments, see e.g. Pliickthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

By "antigen binding domain" herein is meant the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

By "variable region" or "variable domain" herein is meant the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

By "hypervariable region" or "HVR" herein is meant each of the regions of an antibody variable domain which are hypervariable in sequence and/or form structurally defined loops "hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The antibody of the present invention can be chimeric antibodies, humanized antibodies, human antibodies, or antibody fusion proteins.

By "chimeric antibody" herein is meant a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a subhuman primate, cat or dog.

By "humanized antibody" herein is meant a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody. In some embodiments, specific residues of the framework region of the humanized antibody, particularly those that are touching or close to the CDR sequences, may be modified, for example replaced with the corresponding residues from the original rodent, subhuman primate, or other antibody.

By "human antibody" herein is meant an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al, Nature Genet. 7: 13 (1994), Lonberg et al, Nature 368:856 (1994), and Taylor et al, Int. Immun 6:579 (1994). A fully human antibody also can be constructed by genetic or chromosomal transfection methods, as well as phage display technology, all of which are known in the art. See for example, McCafferty et al, Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated herein by reference in their entirety.

By "antibody fusion protein" herein is meant a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

In some embodiments, the targeting moiety comprises a probody, such as those disclosed in U.S. Pat. Nos. 8,518, 404; 8,513,390; and US Pat. Appl. Pub. Nos.; 20120237977A1, 20120149061A1, 20130150558A1, the disclosures of which are incorporated by reference in their entireties.

Probodies are monoclonal antibodies that are selectively activated within the cancer microenvironment, focusing the activity of therapeutic antibodies to tumors and sparing healthy tissue.

In general, the probody comprises at least an antibody or antibody fragment thereof (collectively referred to as "AB"), capable of specifically binding a target, wherein the AB is modified by a masking moiety (MM). When the AB is modified with a MM and is in the presence of the target, specific binding of the AB to its target is reduced or inhibited, as compared to the specific binding of the AB not modified with an MM or the specific binding of the parental AB to the target. The dissociation constant (Kd) of the MM towards the AB is generally greater than the Kd of the AB towards the target. When the AB is modified with a MM and is in the presence of the target, specific binding of the AB to its target can be reduced or inhibited, as compared to the specific binding of the AB not modified with an MM or the specific binding of the parental AB to the target. When an AB is coupled to or modified by a MM, the MM can 'mask' or reduce, or inhibit the specific binding of the AB to its target. When an AB is coupled to or modified by a MM, such coupling or modification can effect a structural change which reduces or inhibits the ability of the AB to specifically bind its target.

In some embodiments, the probody is an activatable antibodies (AAs) where the AB modified by an MM can further include one or more cleavable moieties (CM). Such AAs exhibit activatable/switchable binding, to the AB's target. AAs generally include an antibody or antibody fragment (AB), modified by or coupled to a masking moiety (MM) and a modifiable or cleavable moiety (CM). In some embodiments, the CM contains an amino acid sequence that serves as a substrate for a protease of interest. In other embodiments, the CM provides a cysteine-cysteine disulfide bond that is cleavable by reduction. In yet other embodiments the CM provides a photolytic substrate that is activatable by photolysis.

The CM and AB of the AA may be selected so that the AB represents a binding moiety for a target of interest, and the CM represents a substrate for a protease that is co-localized with the target at a treatment site in a subject. Alternatively, or in addition, the CM is a cysteine-cysteine disulfide bond that is cleavable as a result of reduction of this disulfide bond. AAs contain at least one of a protease-cleavable CM or a cysteine-cysteine disulfide bond, and in some embodiments include both kinds of CMs. The AAs can alternatively or further include a photolabile substrate, activatable by a light source. The AAs disclosed herein find particular use where, for example, a protease capable of cleaving a site in the CM is present at relatively higher levels in target-containing tissue of a treatment site (for example diseased tissue; for example, for therapeutic treatment or diagnostic treatment) than in tissue of non-treatment sites (for example in healthy tissue). The AAs disclosed herein also find particular use where, for example, a reducing agent capable of reducing a site in the CM is present at relatively higher levels in target-containing tissue of a treatment or diagnostic site than in tissue of non-treatment non-diagnostic sites. The AAs disclosed herein also find particular use where, for example, a light source, for example, by way of laser, capable of photolysing a site in the CM is introduced to a target-containing tissue of a treatment or diagnostic site.

In some embodiments, AAs can provide for reduced toxicity and/or adverse side effects that could otherwise result from binding of the AB at non-treatment sites if the AB were not masked or otherwise inhibited from binding its target. Where the AA contains a CM that is cleavable by a reducing agent that facilitates reduction of a disulfide bond, the ABs of such AAs may selected to exploit activation of an AB where a target of interest is present at a desired treatment site characterized by elevated levels of a reducing agent, such that the environment is of a higher reduction potential than, for example, an environment of a non-treatment site.

In general, an AA can be designed by selecting an AB of interest and constructing the remainder of the AA so that, when conformationally constrained, the MM provides for masking of the AB or reduction of binding of the AB to its target. Structural design criteria to be taken into account to provide for this functional feature.

In some embodiments, the targeted therapeutic is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art can be used in the compositions of the invention, in particular for the treatment of the disease with which the target antigen is associated. Examples of target antigens (and their associated diseases) to which a target therapeutic of the invention can be targeted include: CD2, CD19, CD20, CD22, CD27, CD33, CD37, CD38, CD40, CD44, CD47, CD52, CD56, CD70, CD79, CD137, 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING, Syndecan-1, TALI, TAG-72, Tenascin, TIM3, TRAILR1, TRAILR2, VEGFR-1, VEGFR-2, VEGFR-3.

In some embodiments, the antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Opdivo (nivolumab), Dacetuzumab, Urelumab, Tecentriq (atezolizumab, MPDL3280A), Lambrolizumab, Blinatumomab, CT-011, Keytruda (pembrolizumab, MK-3475), BMS-936559, MED14736, MSB0010718C, Imfinzi (durvalumab), Bavencio (avelumab) and margetuximab (MGAH22).

In some embodiments, the anti-HER2 antibody is trastuzumab (Herceptin), pertuzumab or margetuximab (MGAH22). Both trastuzumab and pertuzumab are monoclonal antibodies that have anti-tumor activities against HER2 positive tumor or cancer cells. Margetuximab (or MGAH22) is a next-generation, Fc-optimized monoclonal antibody (mAb) that targets HER2. Clinical trials have shown that margetuximab is effective for the tumor or cancer cells that express moderate levels of HER2.

Herceptin (Trastuzumab) is a humanized monoclonal antibody that acts on human epidermal growth factor receptor extracellular domain of Her2, which is expressed in 25%-30% of breast cancer. It is believed that Trastuzumab has anti-tumor effect through (1) down-regulation Her2 receptor, inhibition of Her2 intracellular signaling transduction pathways and induction of apoptosis; (2) immune mechanisms related antibody dependent ADCC and CDC to kill tumor cells; (3) enhance the effects of chemotherapy.

In some embodiments, the anti-EGFR antibody is Cetuximab, Panitumumab, necitumumab, Matuzumab Nimotuzumab, Zalutumumab, RO5083945, MDX447, or MEHD7945. These antibodies bind to EGFR and inhibit signaling transduction pathway that activates the tumor cell division, proliferation and growth.

Erbitux (Cetuximab) is a chimeric antibody that acts on epidermal growth factor receptor (EGFR). Erbitux binds EGFR to inhibit its signal transduction pathway, affecting cell proliferation, invasion and metastasis, and angiogenesis. Inhibition of EGFR signal transduction pathway can enhance chemotherapy drugs and radiation therapy efficacy.

In some embodiments, the anti-CD20 antibody is selected from the group consisting of: rituximab, ofatumumab, veltuzumab, ocrelizumab, AME-133v, PRO131921, GA101, Ibritumomab tiuxetan, tositumomab, and TRU-015.

Rituximab, the first generation CD20 mAb, can induce complement-dependent cytotoxicity (CDC) and antibody-dependent cellular cytotoxicity (ADCC), leading to its clinical activity against lymphoma cells. CDC represents the primary mechanism for cell-killing by rituximab. However, some lymphoid cells (i.e. 10% of CLL cells) were resistant to CDC because of lower levels of complement activation or decreased cytotoxicity of activated complements. In addition, rituximab can lead to apoptosis of B cells upon binding to CD20 and therefore can directly inhibit cell growth. Recently, a novel mechanism of cell killing by mAbs was reported to involve reactive oxygen species mediated through NADPH.

The "rituximab" antibody is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137.

Rituxan (Rituximab) is a chimeric antibody used for the treatment of B-cell non-Hodgkin's lymphoma. It acts on the surface of B cells expressing the CD20 antigen that is expressed on 90% of B-cell non-Hodgkin's lymphoma. Rituxan binds CD20 to induce B cell lysis through CDC and ADCC, as well as sensitize human lymphocytes that are drug resistance for some cytotoxic chemotherapeutics.

The second-generation anti-CD20 mAbs include ofatumumab, veltuzumab, and ocrelizumab. These are humanized to reduce immunogenicity.

Ofatumumab ((Genmab) is a fully human type I anti-CD20 IgG1kappa mAb. Ofatumumab binds to both the small and large extracellular loops (ECL) of CD20 molecule, and is more effective than rituximab at killing target cells. It has been shown to be more potent than rituximab against both rituximab-sensitive and resistant cells. Its activity against rituximab-resistant cells and the potent CDC effect are believed to be due to the proximal epitope of the small loop of CD20 molecule and the high capacity for C1q activation. Ofatumumab (arzerra) has been approved for treatment of relapsed or refractory CLL who have failed fludarabine and alemtuzumab (FA-ref). Ofatumumab is given IV weekly on a fixed dose, 300 mg for dose 1, and 2000 mg weekly×7 in subsequent doses. This is followed by every four weeks for 4 more doses.

Ocrelizumab (PRO70769) (Genentech/Roche/Biogen) is another type I second generation humanized mAb that differs from rituximab at several amino acid positions within the CDRs of the light chain and heavy chain variable regions. With enhanced efficacy toward lymphoid malignancies and increased binding affinity for the low-affinity variants of the FcγRIIIa receptor (CD16), this mAb has increased ADCC and lower CDC activity compared with rituximab.

Veltuzumab (IMMU-106, hA20) has more potent binding avidities and a stronger effect on CDC than rituximab. Veltuzumab is a humanized, type I anti-CD20 IgG1 mAb, engineered recombinantly with complementarity-determining regions (CDRs) identical to rituximab, except for a single amino acid change, Asp101 instead of Asn101, in the CDR3 of the variable heavy chain. This modification results in significantly slower off-rates and increased CDC cytotoxicity in three human lymphoma cell lines.

The third-generation humanized CD-20 mAbs have an engineered Fc region to increase their binding affinity for the FcγRIIIa receptor. There at least three third-generation mAbs, AME-133v, PRO131921 and GA101.

AME-133v (LY2469298, ocaratuzumab) (Applied Molecular Evolution/Eli Lilly), is a type I, humanized IgG1 mAb. Its binding affinity to CD20 has a 13 to 20-fold increase with 5 to 7-fold higher avidity to the low-affinity (F/F and F/V) variants of FcγRIIIa receptor. These may have been the mechanisms to overcome the lower response rates and shorter duration of responses to rituximab.

PRO131921 (Genentech), is a humanized IgG1 (ocrelizumab) with modified Fc for enhanced CDC and ADCC activities over rituximab.

GA101 (R05072759, obinutuzumab) (Glycart/Roche), is a fully humanized, type II, IgG1 mAb derived from humanization of the parental B-Ly1 mouse antibody and subsequent glycoengineering of Fc region. GA101 binds CD20 through a totally different orientation than rituximab and over a larger epitope. It appears to have more potent activity through direct killing as well as NK-cell mediated ADCC effect. GA101 was shown to have activity in rituximab-resistant cell lines.

In some embodiments, the anti-PD-1 antibody is MK-3475 (formerly lambrolizumab, Merck), AMP-514, AMP-224 (MedImmune/AstraZeneca), BMS-936558 (MDX-1106, Bristol-Myers Squibb), or CT-011 (Curetech).

Pembrolizumab (MK-3475) is a humanized, monoclonal anti-PD-1 antibody designed to reactivate anti-tumor immunity. Pembrolizumab exerts dual ligand blockade of the PD-1 pathway by inhibiting the interaction of PD-1 on T cells with its ligands PD-L1 and PD-L2.

In some embodiments, the anti-PD-1 antibody is one of the antibodies disclosed in U.S. Pat. Nos. 8,354,509, and 8,168,757, the disclosure of which is incorporated by reference in their entirety.

Nivolumab (also known as BMS-936558 or MDX1106, is a fully human IgG4 monoclonal antibody developed by Bristol-Myers Squibb for the treatment of cancer.

In some embodiments, the anti-PD-1 antibody is one of the antibodies disclosed in WO2004/056875, U.S. Pat. Nos. 7,488,802 and 8,008,449, the disclosure of which is incorporated by reference in their entirety.

AMP-514 and AMP-224 are an anti-programmed cell death 1 (PD-1) monoclonal antibody (mAb) developed by Amplimmune, which was acquired by MedImmune.

In some embodiments, the anti-PD-1 antibody is one of the antibodies disclosed in US Appl. Pub. No. 20140044738, the disclosure of which is incorporated by reference in their entirety.

In some embodiments, the six CDRs are: (A) the three light chain and the three heavy chain CDRs of anti-PD-1 antibody 1E3; (B) the three light chain and the three heavy chain CDRs of anti-PD-1 antibody 1E8; or (C) the three light chain and the three heavy chain CDRs of anti-PD-1 antibody 1H3.

Pidilizumab (CT-011) is an anti-PD-1 monoclonal antibody developed by Israel-based Curetech Ltd.

In some embodiments, the anti-PD-1 antibody is one of the antibodies disclosed in US Pat. Appl. Pub. Nos. 20080025980 and 20130022595, the disclosure of which is incorporated by reference in their entirety.

In some embodiments, the anti-PD-L1 antibody is MPDL3280A and YW243.55.570, (Genentech/Roche), MEDI-4736 (MedImmune/AstraZeneca), BMS-936559 (MDX-1105, Bristol-Myers Squibb), and MSB0010718C (EMD Serono/Merck KGaA).

MPDL3280A (Tecentriq, Genentech) is an engineered anti-PD-L1 antibody designed to target PD-L1 expressed on tumor cells and tumor-infiltrating immune cells. MPDL3280A is designed to prevent PD-L1 from binding to PD-1 and B7.1. This blockade of PD-L1 may enable the activation of T cells, restoring their ability to detect and attack tumor cells. MPDL3280A contains an engineered fragment crystallizable (Fc) domain designed to optimize efficacy and safety by minimizing antibody-dependent cellular cytotoxicity (ADCC).

In some embodiments, the anti-PD-L1 antibody is one of the antibodies disclosed in U.S. Pat. No. 7,943,743, the disclosure of which is incorporated by reference in their entirety.

BMS-936559 (MDX-1105, Bristol-Myers Squibb) is a fully human IgG4 anti-PD-L1 mAb that inhibits the binding of the PD-L1 ligand to both PD-1 and CD80.

In some embodiments, the anti-PD-L1 antibody is one of the antibodies disclosed in U.S. Pat. No. 7,943,743, the disclosure of which is incorporated by reference in their entirety.

MSB0010718C (EMD Serono of Merck KGaA) is fully human IgG1 monoclonal antibody that binds to PD-L1.

In some embodiments, the anti-PD-L1 antibody is one of the antibodies disclosed in WO 2013079174 A1, the disclosure of which is incorporated by reference in their entirety.

MEDI4736 (MedImmune/AstraZeneca) is a human IgG1 antibody which binds specifically to PD-L1, preventing binding to PD-1 and CD80.

In some embodiments, the anti-PD-L1 antibody is one of the antibodies disclosed in WO 2011066389 A1 and U.S. Pat. No. 8,779,108, the disclosure of which is incorporated by reference in their entirety.

In some embodiments, the anti-PD-L1 antibody is one of the antibodies disclosed in U.S. Pat. No. 8,552,154, the disclosure of which is incorporated by reference in their entirety.

Avastin (Bevacizumab) is a humanized monoclonal antibody that targets vascular endothelial growth factor (VEGF). Its binding of VEGFR inhibits VEGF and signal transduction, resulting in inhibition of tumor angiogenesis.

Other antibodies that currently under development can also be used as targeted therapeutic. For example, therapeutic monoclonal antibodies against the following targets are under development for treatment of tumors: CD2, CD19, CD20, CD22, CD27, CD33, CD37, CD38, CD40, CD44, CD47, CD52, CD56, CD70, CD79, and CD137 and the following targets for treatment of tumors: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING, Syndecan-1, TAL1, TAG-72, Tenascin, TIM3, TRAILR1, TRAILR2, VEGFR-1, VEGFR-2, and VEGFR-3 and their variant. (Scott A M, Wolchok J D, Old L J. Antibody Therapy of Cancer. Nat Rev Cancer. 2012 Mar. 22; 12(4): 278-87).

In some embodiments, the targeted therapeutic comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

III. Pharmaceutical Formulations and Administration

The present invention further relates to a pharmaceutical formulation comprising a compound of the invention or a pharmaceutically acceptable salt thereof, and one or more pharmaceutically acceptable carriers.

The compounds described herein including pharmaceutically acceptable carriers such as addition salts or hydrates thereof, can be delivered to a patient using a wide variety of routes or modes of administration. Suitable routes of administration include, but inhalation, transdermal, oral, rectal, transmucosal, intestinal and parenteral administration, including intramuscular, subcutaneous and intravenous injections. Preferably, the compounds of the invention comprising an antibody or antibody fragment as the targeting moiety are administered parenterally, more preferably intravenously.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); Ca+2 antagonists (e.g., verapamil, nifedipine, nitrendipine and caroverine); amphotericin; triparanol analogues (e.g., tamoxifen); antiarrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, and suspensions for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include calcium carbonate, calcium phosate, various sugars, starches, cellulose derivatives, gelatin, and polymers such as polyethylene glycols.

A preferred pharmaceutical composition is a composition formulated for injection such as intravenous injection and includes about 0.01% to about 100% by weight of the compound of the present invention, based upon 100% weight of total pharmaceutical composition. The drug-ligand conjugate may be an antibody-cytotoxin conjugate where the antibody has been selected to target a particular cancer.

In some embodiments, the pharmaceutical composition of the present invention further comprises a second chemotherapeutic agent.

By "chemotherapeutic agent" herein is meant a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin.

In some embodiments, the second chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

IV. Kits of the Invention

In another aspect, the present invention provides kits. In certain embodiments, the kits of the invention comprise one or more containers comprising a composition or compound provided herein. The kits may further comprise a suitable set of instructions, generally written instructions, relating to the use of the composition for the intended treatment (e.g., immunomodulation, ameliorating symptoms of an infectious disease, treatment of tumor, increasing IFN-γ levels, increasing IFN-α levels, or ameliorating an IgE-related disorder).

The kits may comprise the composition provided herein packaged in any convenient, appropriate packaging. For example, if the composition is a dry formulation (e.g., freeze dried or a dry powder), a vial with a resilient stopper is normally used, so that the composition may be easily resuspended by injecting fluid through the resilient stopper. Ampoules with non-resilient, removable closures (e.g., sealed glass) or resilient stoppers are most conveniently used for liquid formulations of composition. Also contemplated are packages for use in combination with a specific device, such as an inhaler, nasal administration device (e.g., an atomizer) or an infusion device such as a minipump.

The instructions relating to the use of composition generally include information as to dosage, dosing schedule, and route of administration for the intended treatment. The containers of composition may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

V. Medical Use

In another aspect, the present invention provides a method for treating a disease condition in a subject that is in need of such treatment, comprising: administering to the subject a pharmaceutical composition comprising a therapeutically effective amount of the compound of the present invention a pharmaceutically acceptable salt thereof, and a pharmaceutical acceptable carrier.

In addition to the compositions and constructs described above, the present invention also provides a number of uses of the compounds of the invention. Uses of the compounds of the current invention include: killing or inhibiting the growth or replication of a tumor cell or cancer cell, treating cancer, treating a pre-cancerous condition, preventing the multiplication of a tumor cell or cancer cell, preventing cancer, preventing the multiplication of a cell that expresses an auto-immune antibody. These uses comprise administering to an animal such as a mammal or a human in need thereof an effective amount of a compound of the present invention.

The compound of the current invention is useful for treating diseases such as cancer in an animal, such as a human being. Compositions and uses for treating tumors by providing a subject the composition in a pharmaceutically acceptable manner, with a pharmaceutically effective amount of a composition of the present invention are provided.

By "cancer" herein is meant the pathological condition in humans that is characterized by unregulated cell proliferation. Examples include but are not limited to: carcinoma, lymphoma, blastoma, and leukemia. More particular examples of cancers include but are not limited to: lung (small cell and non-small cell), breast, prostate, carcinoid, bladder, gastric, pancreatic, liver (hepatocellular), hepatoblastoma, colorectal, head and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML).

By "inhibiting" or "treating" or "treatment" herein is meant to reduction, therapeutic treatment and prophylactic or preventative treatment, wherein the objective is to reduce or prevent the aimed pathologic disorder or condition. In one example, following administering of a compound of the present invention, a cancer patient may experience a reduction in tumor size. "Treatment" or "treating" includes (1) inhibiting a disease in a subject experiencing or displaying the pathology or symptoms of the disease, (2) ameliorating a disease in a subject that is experiencing or displaying the pathology or symptoms of the disease, and/or (3) affecting any measurable decrease in a disease in a subject or patient that is experiencing or displaying the pathology or symptoms of the disease. To the extent a compound of the present invention may prevent growth and/or kill cancer cells, it may be cytostatic and/or cytotoxic.

By "therapeutically effective amount" herein is meant an amount of a compound provided herein effective to "treat" a disorder in a subject or mammal. In the case of cancer, the therapeutically effective amount of the drug may either reduce the number of cancer cells, reduce the tumor size, inhibit cancer cell infiltration into peripheral organs, inhibit tumor metastasis, inhibit tumor growth to certain extent, and/or relieve one or more of the symptoms associated with the cancer to some extent.

Administration "in combination with" one or more further therapeutic agents includes simultaneous (concurrent) and consecutive administration in any order. As used herein, the term "pharmaceutical combination" refers to a product obtained from mixing or combining active ingredients and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

In some embodiments, the diseases condition is tumor. In some embodiments, the disease condition comprises abnormal cell proliferation, such as a pre-cancerous lesion.

The current invention is particularly useful for the treatment of cancer and for the inhibition of the multiplication of a tumor cell or cancer cell in an animal Cancer, or a precancerous condition, includes a tumor, metastasis, or any disease or disorder characterized by uncontrolled cell growth, can be treated or prevented by administration the drug-ligand complex of the current invention. The compound delivers the activating moiety to a tumor cell or cancer cell. In some embodiments, the targeting moiety specifically binds to or associates with a cancer-cell or a tumor-cell-associated antigen. Because of its close proximity to the ligand, after being internalized, the activating moiety can be taken up inside a tumor cell or cancer cell through, for example, receptor-mediated endocytosis. The antigen can be attached to a tumor cell or cancer cell or can be an extracellular matrix protein associated with the tumor cell or cancer cell. Once inside the cell, the linker is hydrolytically or enzymatically cleaved by a tumor-cell or cancer-cell-associated proteases, thereby releasing the activating moiety. The released activating moiety is then free to diffuse and induce or enhance immune activity of immune cells or tumor cells. In an alternative embodiment, the activating moiety is cleaved from the compound tumor microenvironment, and the drug subsequently penetrates the cell.

Representative examples of precancerous conditions that may be targeted by the compounds of the present invention, include: metaplasia, hyperplysia, dysplasia, colorectal polyps, actinic ketatosis, actinic cheilitis, human papillomaviruses, leukoplakia, lychen planus and Bowen's disease.

Representative examples of cancers or tumors that may be targeted by compounds of the present invention include: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemia. It will be readily apparent to the ordinarily skilled artisan that the particular targeting moiety used in the compound can be chosen such that it targets the activating moiety to the tumor tissue to be treated with the drug (i.e., a targeting agent specific for a tumor-specific antigen is chosen). Examples of such targeting moiety are well known in the art, examples of which include anti-Her2 for treatment of breast cancer, anti-CD20 for treatment of lymphoma, anti-PSMA for treatment of prostate cancer and anti-CD30 for treatment of lymphomas, including non-Hodgkin's lymphoma.

Thus, the present invention provides methods for the synergistic treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

Most preferably, the invention is used to treat accelerated or metastatic cancers of the bladder, pancreatic cancer, prostate cancer, non-small cell lung cancer, colorectal cancer, and breast cancer.

In a preferred embodiment of this invention, a method is provided for the synergistic treatment of cancerous tumors. Advantageously, the synergistic method of this invention reduces the development of tumors, reduces tumor burden, or produces tumor regression in a mammalian host.

In some embodiments, the abnormal proliferation is of cancer cells.

In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

In some embodiments, the present invention provides a compound for use in killing a cell. The compound is administered to the cell in an amount sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

In another aspect, the present compositions provided herein is used for treating an autoimmune disease condition in a subject or individual that is in need of such treatment.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MvS), immune-mediated infertility such as premature ovarian failure, scleroderma. Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S e/al., eds., New York: McGraw-Hill, 1998.

The systemic disease SLE is characterized by the presence of antibodies to antigens that are abundant in nearly every cell, such as anti-chromatin antibodies, anti-spliceosome antibodies, anti-ribosome antibodies and anti-DNA antibodies. Consequently, the effects of SLE are seen in a variety of tissues, such as the skin and kidneys. Autoreactive T cells also play a role in SLE. For example, studies in a murine lupus model have shown that non-DNA nucleosomal antigens, e.g. histones, stimulate autoreactive T cells that can drive anti-DNA producing B cells. Increased serum levels of IFN-$\alpha$ has been observed in SLE patients and shown to correlate with both disease activity and severity, including fever and skin rashes, as well as essential markers associated with the disease process (e.g., anti-dsDNA antibody titers). It has also been shown that immune complexes present in the circulation could trigger IFN-$\alpha$ in these patients and, thus, maintain this chronic presence of elevated IFN-$\alpha$. Two different types of immune complexes have been described to trigger IFN-$\alpha$ from human PDC: DNA/anti-DNA antibody complexes and RNA/anti-ribonucleoprotein-RNA antibody complexes. Because DNA is a ligand of TLR-9 and RNA a ligand for TLR-7/8, it is expected that these two pathways utilize TLR-9 and TLR-7/8 signalling, respectively, in order to chronically induce IFN-$\alpha$ and thus participate in the etiopathogenesis of SLE. Accordingly, IRP and/or IRC compositions which are effective in inhibiting TLR-7/8 and TLR-9 responses may be particularly effective in treating SLE.

In some embodiments, the autoimmune disease is selected from the group consisting of: Lupus erythematosus, Multiple sclerosis, Rheumatoid arthritis, Psoriasis, Scleroderma, and Sjöogren's syndrome.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 30%, 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug). Preferably, the antibody with drug conjugates retards growth of the tumor when administered in the daily dosage amount over a period of at least five days.

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims

EXAMPLES

The present invention is further exemplified, but not limited, by the following and Examples that illustrate the preparation of the compounds of the invention.

Example 1

CpG Oligonucleotides.

CpG-ODNs were synthesized by Suzhou Ruibo Biotech Ltd. CpG 1-12 were the sequences modified. A type CpG2216 (5'-ggGGGACGATCGTCgggggG-3' SEQ ID NO.:13), B type CpG 2006 (5'-TCGTCGTTTTGTCGTTTTGTCGTT-3, SEQ ID NO.: 14) and CpG 684 (5'-TCgACgTTCgTCgTTCgTCgTTC-3', SEQ ID NO.: 15), and C type CpG2395 (5' tcgtcgttttcggcgcgcgccg-3', SEQ ID NO.: 1617) were used as positive controls. GC-ODN (5'-tggc-caagcttgggccccttgcaagggcc-3' SEQ ID No.:18) was used as negative controls. All of CpG-ODN were dissolved in sterilized water without endotoxin (InvivoGen, America), kept at −40° C. until use.

Leukocytes Concentrated from Human Peripheral Blood and Experimental Animals.

Leukocytes concentrated from human peripheral blood were obtained from Changchun Blood Bank Centre.

Mice and Cell Lines.

Female BALB/c mice (6-8 weeks old) were purchased from Changchun Biological Products Company (China), and all animal experiments were performed according to protocols approved by the Institutional Animal Care and Use Committee at The University of Jilin. Spleen cells from BALB/c mice were cultured in RPMI-1640 medium (Corning, USA) supplemented with 10% fetal bovine serum (Clark, China) and 100 IU/mL penicillin and 100 µg/mL streptomycin (Hyclone, USA) at 37° C. in an incubator with 5% CO2.

Isolation of hPBMCs.

Human peripheral blood mononuclear cells (hPBMCs) were isolated from human peripheral blood using Ficoll density gradient centrifugation. Briefly, the blood was diluted with two times of phosphate-buffered saline (PBS). Diluted blood was layered over the Ficoll (Axis-Shield, Norway) at 1:1, followed by gradients centrifugation at 2,800 rpm for 20 min at room temperature with speeding up at 8 and slowing down at 0. The hPBMCs interface was carefully collected by pipetting and washed with PBS by centrifugation at 1,500 rpm for 5 min. Obtained hPBMCs were cultured in RPMI-1640 medium (Corning, USA) supplemented with 10% human serum (Equitech-Bio, USA) and 100 IU/mL penicillin and 100 µg/mL streptomycin (Hyclone, USA) at 37° C. in an incubator with 5% $CO_2$.

Proliferation Assays.

Cells proliferation was determined by Carboxy fluorescein diacetate succinimidyl ester (CFSE) assay. The cells, at a concentration of ~$10^7$ cells/ml, were suspended in 1 ml PBS. hPBMCs were treated with 9 μM CFSE (Invitrogen, USA) and the mouse spleen cells were treated with 6.3 μM CFSE. Scale up accordingly if performing more cells at one time. Set the cells stand for 7 min in the dark, followed by addition of cold RPMI-1640 medium supplemented with 10% fetal bovine serum to a final volume of 15 ml. Following centrifugation at 1,500 rpm for 5 min, the supernatant was discarded. The cells were resuspended in RPMI-1640 culture medium, with 10% FBS, 100 IU/mL penicillin, and 100 μg/mL streptomycin, and plated in 96-well plates at $5 \times 10^5$ cells/well. After 1 h, the cells were stimulated with 1 μM CpG ODN. After the cells were incubated in incubator at 37° C., 5% CO2 for 6 (hPBMCs) or 5 (the mouse spleen cells) days, the cells were collected and stained, then analyzed by flow cytometer.

Flow Cytometric Analysis.

hPBMCs and the mouse spleen cells were incubated with or without CpG ODN (1 μM) for 24 h, 48 h and 6 or 5 days, and the cells were suspended in PBS. For activation experiments, the cells stimulated for 24 h and 48 h were stained with the following mAbs: anti-CD3, anti-CD4, anti-CD19, anti-CD69. For Proliferation assays, the cells stimulated for 6 or 5 days were stained with the following mAbs: anti-CD3, anti-CD4 and anti-CD19. After incubation with the respective Abs for 30 min at 4° C., cells were washed twice with PBS and then analyzed by LSRFortessa™ flow cytometer (BD, USA).

ELISA and CBA Assays.

hPBMCs ($5 \times 10^5$ cells/well) and the mouse spleen cells ($1 \times 10^6$ cells/well) were plated in 96-well plate and added CpG ODN, dissolved in Sterile/Endotoxin-free water (InvivoGen, USA), to the cultured cells. Supernatants from cultured were collected after 24 hours and 48 hours. According to the instruction of ELISA kits, the amounts of human IFN-α (Mabtech, Sweden), murine IFN-α (eBioscience, Australia), murine IL-6 (Mabtech, Sweden) and murine TNF-α (Mabtech, Sweden) in the culture supernatants were measured. Briefly, 50 μl samples or recombinant standards were added to 50 μl mixed capture beads and incubated for 1 hours. Then added with 50 μl PE detection reagent for another 2 hours. After washing twice to remove unbound PE detection reagent, detected the samples by flow cytometer FACS Array (BD) and analyzed using FCAP Array software (BD).

TABLE 2

Effect of CpG on regulation and activiation of cytokines

| Sequence Name | Cytokines | | | Activation | | | Summary | |
|---|---|---|---|---|---|---|---|---|
| | IFN-a | TNF-a | IL-6 | CD80 | CD86 | HLA-DR | CpG-A effect | CpG-B effect |
| 2216 | 100 | 70 | 64 | 27 | 49 | 11 | 100.0 | 48.9 |
| 2006 | 2 | 100 | 100 | 100 | 100 | 100 | 2.0 | 100.0 |
| 1018 | 4 | 42 | 81 | 18 | 23 | 56 | 3.5 | 41.9 |
| GC-ODN | 0 | 7 | 10 | 28 | 57 | 1 | 0.2 | 9.9 |
| CpG 2 | 49 | 138 | 174 | 86 | 114 | 94 | 48.7 | 114.2 |
| CpG 3 | 60 | 131 | 188 | 80 | 134 | 87 | 59.6 | 130.6 |
| CpG 4 | 33 | 122 | 162 | 68 | 110 | 78 | 32.8 | 109.5 |
| CpG 5 | 51 | 128 | 168 | 94 | 140 | 73 | 50.8 | 127.8 |
| CpG 6 | 27 | 136 | 161 | 72 | 93 | 73 | 26.7 | 93.0 |

ELISA and CBA Assays.

hPBMCs ($5 \times 10^5$ cells/well) and the mouse spleen cells ($1 \times 10^6$ Table 3 shows that CpG 2 effectively induced activation and proliferation of B cell. Human PBMC ($5 \times 10^5$ cells/well) and murine spleen cells ($1 \times 10^6$ cells/well) were inoculated within 96-well plate containing various CpG (CpG 1-12) at 1 μM, culture controls (RPMI-1640 culture media) and CpG 684 as positive control. After 24 and 48 hours, the cells were collected and stained with anti-CD3, anti-CD4, anti-CD19 and anti-CD69. Then analysis was performed by flow cytometer (mean±SEM, n=3).

TABLE 3

CpG induced activation and proliferation of human and murine B cells respectively

| B cells | HUMAN | | | MURINE | | |
|---|---|---|---|---|---|---|
| | Cell proliferation | Activation (24 h) | Activation (48 h) | Cell proliferation | Activation (24 h) | Activation (48 h) |
| CpG 1 | | | | + | + | + |
| CpG 2 | + | + | | + | + | + |
| CpG 3 | + | + | + | + | + | + |
| CpG 4 | | | + | | + | + |
| CpG 5 | + | | + | | + | + |
| CpG 6 | | + | + | + | | + |
| CpG 7 | | | + | + | + | |

TABLE 3-continued

CpG induced activation and proliferation of human and murine B cells respectively

| B cells | HUMAN | | | MURINE | | |
|---|---|---|---|---|---|---|
| | Cell proliferation | Activation (24 h) | Activation (48 h) | Cell proliferation | Activation (24 h) | Activation (48 h) |
| CpG 8 | | | | + | | |
| CpG 9 | + | + | | + | + | |
| CpG 10 | + | | | | + | |
| CpG 11 | | + | | | + | |
| CpG 12 | + | | | | | |
| CpG2216 | + | | | | | |
| CpG2006 | | | + | | | |
| CpG2395 | | | | | | + |

ELISA and CBA Assays.

hPBMCs ($5\times10^5$ cells/well) and the mouse spleen cells ($1\times10^6$ Table 4 shows that CpG effectively induced activation of CD8+ T cells and CD4+ T cells. Human PBMC ($5\times10^5$ cells/well) and murine spleen cells ($1\times10^6$ cells/well) were inoculated within 96-well plate containing various CpG (CpG 1-12) at 1 μM, culture controls (RPMI-1640 culture media) and CpG 684 as positive control. After 24 and 48 hours, the cells were collected and stained with anti-CD3, anti-CD4, anti-CD19 and anti-CD69. Then analysis was performed by flow cytometer (mean±SEM, n=3).

flank tumors were clearly palpable on day 8, mice were randomly grouped (n=6) and injected into the right tumors (mean=104 mm³) with CpG-6, GC control (Non-CpG ODN control) or vehicle (Phosphate Buffered Saline). Treatment was given once per day on every third day for 5 doses. Body weights of all animals were measured every three days throughout the study. Tumor size was measured every three days with a caliper, and tumor volume was estimated using the formula of volume=length×width×0.5. All data are expressed as mean in mm3+SEM. Animals were sacrificed by carbon dioxide asphyxiation and cervical dislocation

TABLE 4

CpG effectively induced activation of CD8+T cells and CD4+T cells respectively

| | HUMAN T cells | | | | | MURINE | | | |
|---|---|---|---|---|---|---|---|---|---|
| | CD8 T cells | | | CD4 T cells | | CD8 T cells | | CD4 T cells | |
| Name | Cell proliferation | Activation (24 h) | Activation (48 h) | Activation (24 h) | Activation (48 h) | Activation (24 h) | Activation (48 h) | Activation (24 h) | Activation (48 h) |
| CpG 1 | + | | + | | + | | + | | + |
| CpG 2 | | + | | | + | + | + | + | + |
| CpG 3 | + | + | + | ++ | + | + | + | + | + |
| CpG 4 | | + | + | + | + | + | ++ | + | |
| CpG 5 | | + | + | + | + | + | + | | + |
| CpG 6 | + | + | + | + | ++ | + | | | |
| CpG 7 | | | | | | | + | | + |
| CpG 8 | + | + | + | + | | | | | + |
| CpG 9 | + | | | + | | + | | + | |
| CpG 10 | + | | | | | | + | + | |
| CpG 11 | + | + | + | + | + | + | | + | |
| CpG 12 | + | | + | | | | | | |
| CpG2216 | + | | | | + | | | | |
| CpG2006 | | | | | | + | + | | |
| CpG2395 | + | + | | + | | | ++ | | |

Example 2

Efficacy of CpG-6 in Murine CT26 Colorectal Tumor Model

Materials and Methods:

All in-vivo experiments were conducted by Pharmaron, Inc. (Beijing, China) in accordance with protocols approved by its institutional Animal Care and Use Committee. The CT26 murine colon carcinoma model was previously described by Hemmerle T and Neri D (Int. J. Cancer 2014, 134: 467-477). Briefly, 6-8 week old BALB/c female mice from Beijing Vital River Laboratory Animal Technology Co., Ltd. were implanted subcutaneously with $2\times10^5$ or $1\times10^5$ of CT26 tumor cells at right or left flank on day 0 or 4 of the study, respectively, for 2-site tumor development. When the right when tumor volumes exceeded 3,000 mm³ or obvious signs of severe distress and/or pain been observed.

Statistical analysis of difference in tumor volume among the groups was conducted on the data obtained by day 15 post treatment initiation using one-way ANOVA; the differences between overall survival times for comparing groups were analyzed using Log-rank (Mantel-Cox) test in GraphPad Prism 6 software; p<0.05 was considered statistically significant.

Figure 4:
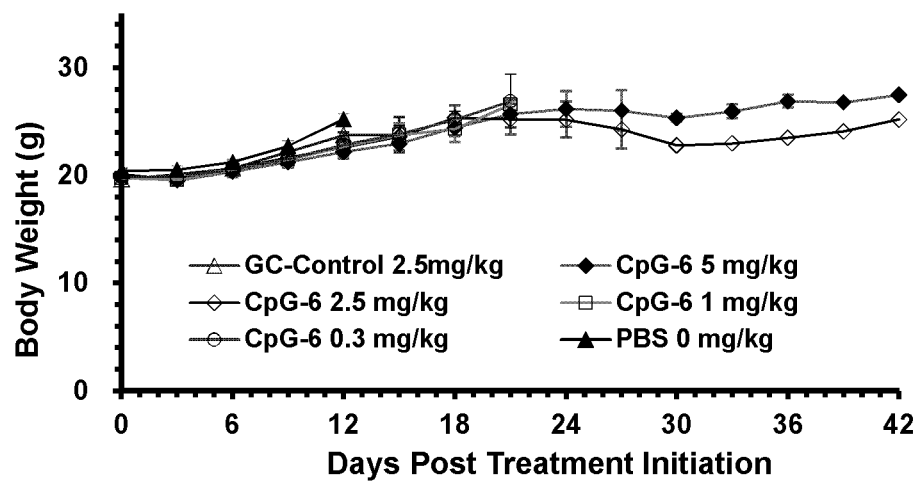
FIG. 4 depicts inhibition effect of intratumoral CpG-6 on CT26 colon carcinoma growth in mice. BALB/c mice were inoculated s.c. on the right flank with $2\times10^5$ CT26 cells on day 0, and on day 4 with $1\times10^5$ cells on the left frank. By day 8 when the right tumors reached approximately 100 mm³ in 6 groups (n=6), mice were randomly injected CpG-6 (0.3-5 mg/kg), GC-control (2.5 mg/kg) or PBS-vehicle into the right flanks, once/day on every third day for 5 doses. Animals were then followed for body weight change (A), tumor growth on right (B) and left (C) flanks, and survival rates (D). All statistical analysis was performed using Prism (GraphPad) software v6.
Figure 4:
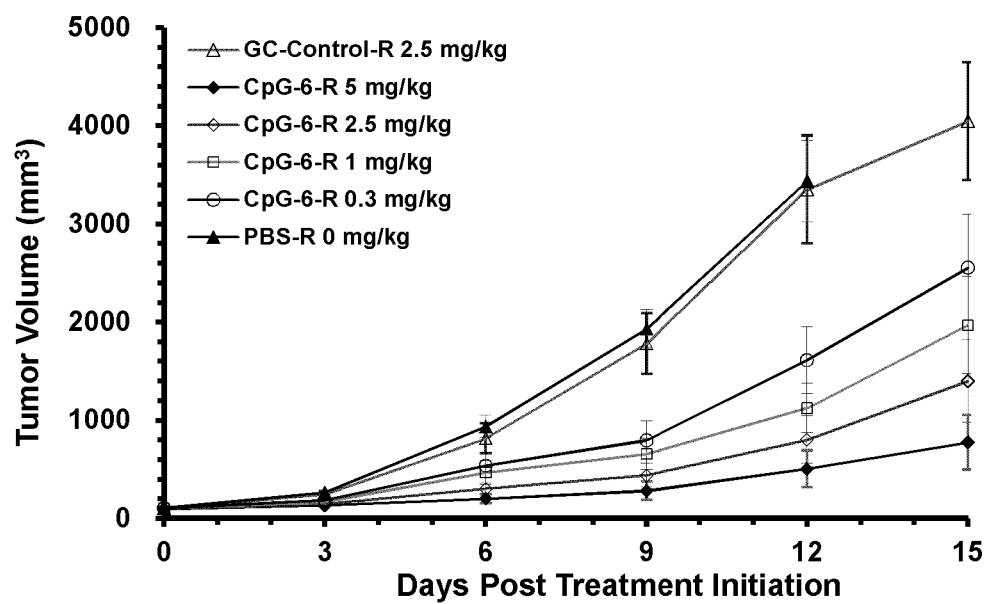
Figure 4:
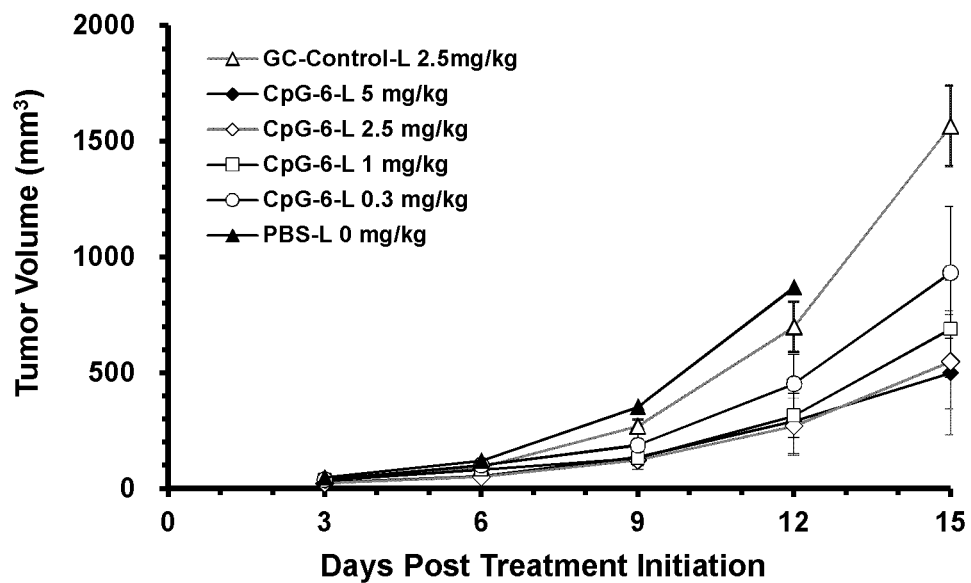
Figure 4:
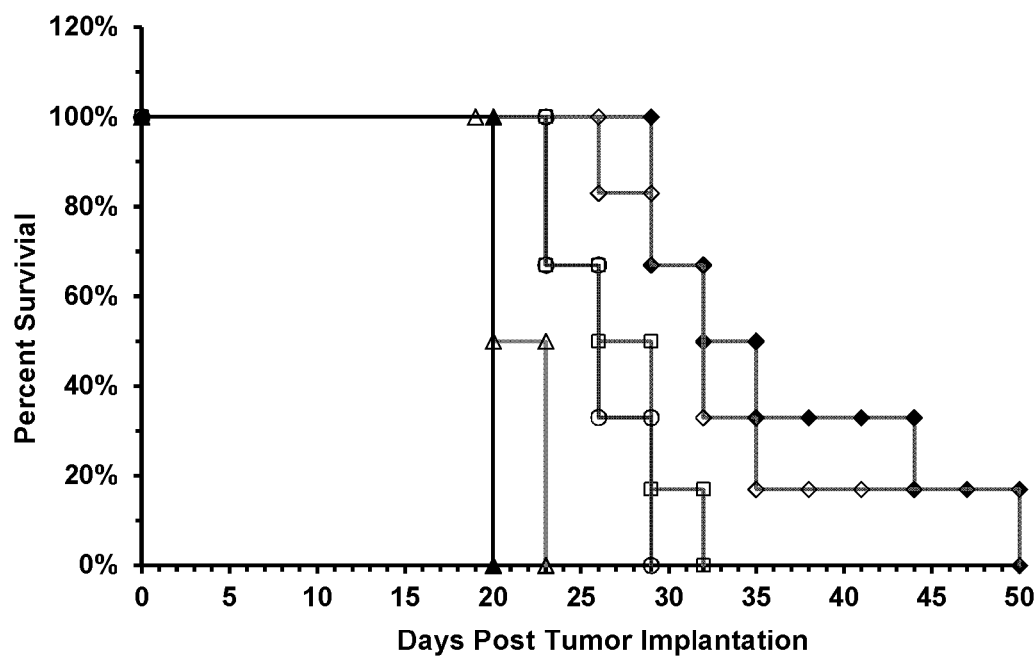

Results:

Inhibition of CT26 tumor growth by intratumal CpG-6 is shown in FIG. 4. A similar tumor growth curve is present for PBS-vehicle group and GC-control (2.5 mg/kg) group, which established its negative control feature as an. non-CpG-ODN (FIG. 4B). In contrast, intratumoral CpG-6 at the same dose level generated a highly significant inhibition of tumor growth (p<0.001). Moreover, CpG-6-mediated anti-tumor effect revealed the dose-dependency as 5 mg/kg group is significantly different from 0.3 mg/kg treated-mice (p=0.009). Similar body weight gains were observed in each six groups over the course of 42-day study period, suggesting well-tolerated intratumoral CpG-6 treatment (FIG. 4A).

TABLE 5

P values between each group by Day 15 (Right flank)

| Group | CpG-6, 5 mg/kg | CpG-6, 2.5 mg/kg | CpG-6, 1 mg/kg | CpG-6, 0.3 mg/kg |
|---|---|---|---|---|
| GC-control | <0.001 | 0.002 | 0.013 | 0.064 |
| CpG-6, 5 mg/kg | — | 0.329 | 0.069 | 0.009 |
| CpG-6, 2.5 mg/kg | — | — | 0.371 | 0.078 |
| CpG-6, 1 mg/kg | — | — | — | 0.359 |

Immune-mediated systemic effect of CpG-6 was also observed on the non-injected CT26 tumor (FIG. 4C). Similar tumor growth curve of the left flank is present in two negative control groups upon intratumoral injection of PBS or GC-control on the right flank. In comparison with its ODN control, administration of CpG-6 into the right flank tumors resulted in a significant suppression of CT26 tumor growth on the left flank of mice (p=0.017 for 2.5 mg/kg). Intratumoral CpG-6 at 5 or 1 mg/kg (p=0.008 or 0.037), but not 0.3 mg/kg (p=0.123), also exhibited a similar efficacy on the left tumor, indicating a dose-dependent systemic effect.

TABLE 6

P values between each group by Day 15 (Left flank)

| Group | CpG-6, 5 mg/kg | CpG-6, 2.5 mg/kg | CpG-6, 1 mg/kg | CpG-6, 0.3 mg/kg |
|---|---|---|---|---|
| GC-control | 0.008 | 0.017 | 0.037 | 0.123 |
| CpG-6, 5 mg/kg | — | 0.686 | 0.405 | 0.123 |
| CpG-6, 2.5 mg/kg | — | — | 0.665 | 0.244 |
| CpG-6, 1 mg/kg | — | — | — | 0.457 |

Overall efficacy of intratumoral CpG-6 is exhibited on the survival of CT26 tumor-bearing mice (FIG. 4D). As negative controls, all animals in PBS or GC-control group were sacrificed by day 23 according to their enlarged tumors over 3000 mm$^3$. In comparison, intratumoral CpG-6 treatment resulted in a significant life prolongation of mice bearing CT26-tumors (2.5 mg/kg, p=0.0009). Whereas all 4 doses of CpG-6 revealed highly significant protection over PBS group (p=0.0009); there is a significant difference between 5 mg/kg and 0.3 mg/kg groups (p=0.005), indicating a dose-responsive effect on the survival of CT26 tumor-bearing mice.

TABLE 7

P values between each group: Log-rank (Mantel-Cox) test

| Group | CpG-6, 5 mg/kg | CpG-6, 2.5 mg/kg | CpG-6, 1 mg/kg | CpG-6, 0.3 mg/kg | PBS |
|---|---|---|---|---|---|
| GC-control | 0.0009 | 0.0009 | 0.0088 | 0.0088 | 0.0555 |
| CpG-6, 5 mg/kg | — | 0.7196 | 0.0189 | 0.0052 | 0.0009 |
| CpG-6, 2.5 mg/kg | — | — | 0.0521 | 0.0136 | 0.0009 |
| CpG-6, 1 mg/kg | — | — | — | 0.4629 | 0.0009 |
| CpG-6, 0.3 mg/kg | — | — | — | — | 0.0009 |

Example 3

Efficacy of CpG-6 in Murine B16F10 Melanoma Tumor Model

Study Objective:

The objective of the study is to evaluate the therapeutic effect of CpG-6 in the treatment of subcutaneous B16F10 Murine Melanoma cancer model in C57BL/6 mice.

Materials and Methods:

All in-vivo experiments were conducted by Pharmaron, Inc. (Beijing, China) in accordance to protocols approved by its institutional Animal Care and Use Committee. The B16F10 murine melanoma model was previously described by Chen S. et. al. (Cancer Immunol Res. 2015, 3: 149-60). Briefly, 6-8 week old C57BL/6 female mice from Beijing HFK Bioscience Co., Ltd. were implanted subcutaneously with 1×10$^5$ or 0.5×10$^5$ of B16F10 tumor cells at right or left flank on day 0 or 4 of the study, respectively, for 2-site tumor development. When the right flank tumors were clearly palpable on day 9, mice were randomly grouped (n=6) and injected into the right tumors (mean~85 mm3) with CpG-6 (0.3-10 mg/kg) or vehicle (Phosphate Buffered Saline). Treatment was given once per day on every other day for 5 doses. Tumor size was measured every three days with a caliper, and tumor volume was estimated using the formula of volume=length×width$^2$×0.5 Animals were sacrificed by carbon dioxide asphyxiation and cervical dislocation when each tumor volume exceeded 3,000 mm3 or obvious signs of severe distress and/or pain been observed.

Statistical analysis of difference on overall survival times for comparing groups were analyzed using Log-rank Mantel-Cox test in GraphPad Prism 6 software; p<0.05 was considered statistically significant.

Figure 1:
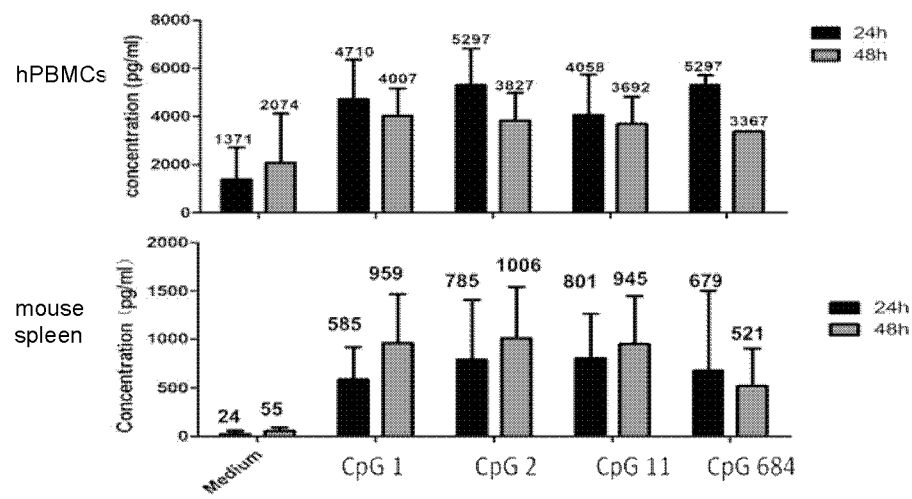
FIG. 1 depicts that IFN-α secretion from pDCs was stimulated by CpG 5 effectively. Human PBMCs (5×105 cells/well) and mouse spleen cells (1×106 cells/well) plated in 96-well plates were cultured for 24 hours and 48 hours with 1 μM different CpG (CpG 3, CpG 5 and CpG 23), medium control (RPMI-1640 medium) and CpG 684 as positive control. Culture supernatants were harvested and the amounts of secreted IFN-α were measured by ELISA or CBA (Mean±SEM, n=3).
Figure 2:
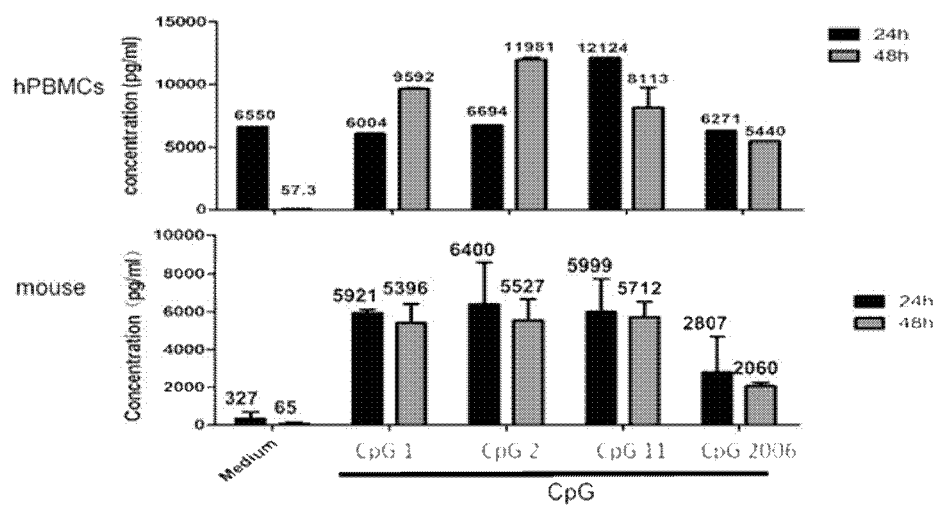
FIG. 2 depicts that IL-6 secretion from B cells was stimulated by CpG 5 effectively. Human PBMCs (5×105 cells/well) and mouse spleen cells (1×106 cells/well) plated in 96-well plates were cultured for 24 hours and 48 hours with 1 μM different CpG (CpG 3, CpG 5 and CpG 23), medium control (RPMI-1640 medium) and CpG 2006 as positive control. Culture supernatants were harvested and the amounts of secreted IL-6 were measured by ELISA or CBA (Mean±SEM, n=3).
Figure 3:
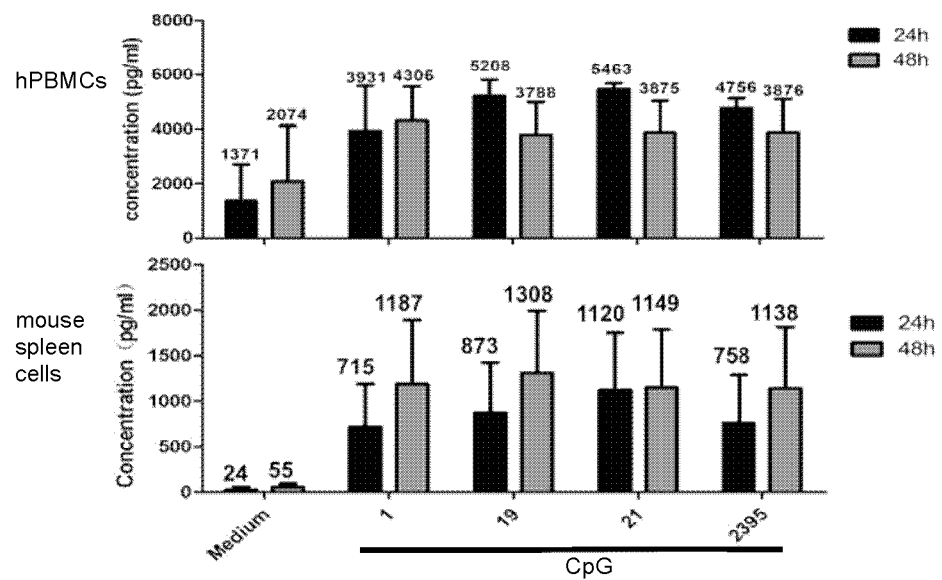
FIG. 3 depicts that IFN-α secretion from pDCs was stimulated by CpG 1 and CpG 10 effectively. Human PBMCs (5×105 cells/well) and mouse spleen cells (1×106 cells/well) plated in 96-well plates were cultured for 24 hours and 48 hours with 1 μM different CpG (CpG 1, CpG 9 and CpG 10), medium control (RPMI-1640 medium) and CpG 2395 as positive control. Culture supernatants were harvested and the amounts of secreted IFN-α were measured by ELISA or CBA (Mean±SEM, n=3).

Results:

Therapeutic effect of intratumoral CpG-6 was assessed on B16F10 melanoma mouse model. In comparison with PBS-vehicle group, which all developed large tumors on the right flank within 20 days; CpG-6-injected tumors exhibited a dose-dependent trend of growth delay, i.e. more tumors at the 10, 3, and 1 mg/kg groups enlarged slowly than the 0.3 mg/kg-treated groups (FIG. 5A1-A4). During the study period, two mice (33%) in PBS-group also developed large tumors on their left flanks; whereas only one animal (4%) in the entire CpG-6-treated groups had enlarged tumor on the non-injected flank (FIG. 5B1-B4). Overall efficacy of CpG-6 administration was demonstrated on the survival of tumor-bearing mice (FIG. 5C). As similar survival curves were observed between PBS vehicle and CpG-6 0.3 mg/kg treated groups, with all mice dead of large tumors around day 29 after B16F10 cell inoculation; CpG-6 intratumoral injection at 10 mg/kg and 3 mg/kg, but not at 1 mg/kg, significantly improved the survival of mice bearing melanoma (p<0.05 vs. PBS).

TABLE 8

P values between each group: Log-rank (Mantel-Cox) test

| Group | CpG-6 10 mg/kg | CpG-6 3 mg/kg | CpG-6 1 mg/kg | CpG-6 0.3 mg/kg |
|---|---|---|---|---|
| PBS | 0.042 | 0.024 | 0.083 | 0.418 |
| CpG-6 10 mg/kg | — | 0.885 | 0.331 | 0.191 |
| CpG-6 3 mg/kg |  | — | 0.580 | 0.085 |
| CpG-6 1 mg/kg |  |  | — | 0.4019 |

Example 4

Combinational Efficacy of CpG-6 and Anti-Neu mAb in Murine TUBO Mammary Tumor Model Materials and Methods:

All in-vivo experiments were conducted at Beijing Vital River Laboratory Animal Technology Co, Ltd. (Beijing, China) in accordance to protocols approved by its institutional Animal Care and Use Committee. The TUBO murine mammary model was previously described by Mortenson E D et. al. (Clin. Cancer Res. 2013, 19: 1476-1486). Briefly, 8-10 week old Balb/c female mice from Beijing Vital River Laboratory Animal Technology Co., Ltd. were implanted subcutaneously with $5 \times 10^5$ TUBO tumor cells at upper right flank on day 0 for the first-round tumor development. When tumors were clearly palpable on day 11, mice were randomly grouped (Table 9). and injected into tumors (60~120 mm3) with CpG-6 (n=24), GC-control (n=6) or PBS-vehicle (n=6), once per day on every third day for 4 doses. In combinational treatment groups, Anti-neu mAb (clone 7.16.4 from Institute of Biophysics, Beijing, China) was administrated intravenously at 10 mg/kg/week for 3 doses.

TABLE 9

1st Inoculation and Treatment

| Group | Treatment | Dose (mg/kg) | Route | Frequency |
|---|---|---|---|---|
| 1 | PBS + PBS | 0 + 0 | i.v. + i.t. right flank | Q7D × 3 + Q3D × 4 |
| 2 | Anti-neu + GC-control | 10 + 2.5 | i.v. + i.t. right flank | Q7D × 3 + Q3D × 4 |
| 3 | Anti-neu + PBS | 10 + 0 | i.v. + i.t. right flank | Q7D × 3 + Q3D × 4 |
| 4 | Anti-neu + CpG-6 | 10 + 2.2 | i.v. + i.t. right flank | Q7D × 3 + Q3D × 4 |

After 53 day study when upper right tumors shrunk to barely palpable (≤30 mm$^3$) in Anti-neu and CpG-6 treated-mice, a second s.c. inoculation was given on their left flanks into two groups (TUBO $5 \times 10^5/0.1$ mL or 4T1 $1 \times 10^5/0.1$ mL). Additional naïve mice (female 3-4 month old, 20-22 g) were employed as controls for tumor development after TUBO or 4T1 inoculation (Table 10)

TABLE 10

2$^{nd}$ Inoculation (Route and Type)

| Groups | mice | N | Tumor type | Route | Tumor cell No |
|---|---|---|---|---|---|
| A | Naïve | 4 | TUBO | s.c. left | $5 \times 10^5/0.1$ mL |
| B | Control | 4 | 4T1 | s.c. left | $1 \times 10^5/0.1$ mL |
| 4.1 | Anti-neu + | 12 | TUBO | s.c. left | $5 \times 10^5/0.1$ mL |
| 4.2 | CpG-6 | 11 | 4T1 | s.c. left | $1 \times 10^5/0.1$ mL |

On study day 112, when all naïve mice were dead of tumor growth, a third tumor cell inoculation (TUBO $5 \times 10^5/0.1$ mL or 4T1 $1 \times 10^5/0.1$ mL correspondingly) was delivered s.c. around lower right flank of all living mice treated with CpG-6 and Anti-neu previously. Once again a new set of naïve BALB/c mice (Female 6-7 month old, 24-35 g) were used as controls for tumor development following TUBO or 4T1 inoculation (Table 11).

TABLE 11

3$^{rd}$ Inoculation (Route and Type)

| Groups | mice | N | Tumor type | Route | Tumor Cell No |
|---|---|---|---|---|---|
| C | Naïve | 4 | TUBO | s.c. low left | $5 \times 10^5/0.1$ mL |
| D | Control | 4 | 4T1 | s.c. low left | $1 \times 10^5/0.1$ mL |
| 4.1 | Anti-neu + | 12 | TUBO | s.c. low left | $5 \times 10^5/0.1$ mL |
| 4.2 | CpG-6 | 6 | 4T1 | s.c. low left | $1 \times 10^5/0.1$ mL |

Body weights of all animals were measured every three days throughout the study. Body weight change (%) was calculated using the formula of BW change (%)=(BW Day X/BW Day 0)×100. Tumor size was measured every three days with a caliper, and tumor volume was estimated using the formula of volume=length×width×0.5. All data are expressed as mean in mm$^3$+SEM Animals were sacrificed by carbon dioxide asphyxiation and cervical dislocation when each tumor volume exceeded 3,000 mm$^3$ or obvious signs of severe distress and/or pain been observed.

Statistical analysis was performed to compare the tumor growth between groups by two-way analysis of variance (ANOVA) or unpaired t test as indicated. The differences between overall survival times of comparing groups were analyzed using Log-rank (Mantel-Cox) test and Gehan-Breslow-Wilcoxon test in GraphPad Prism 6 software; p<0.05 was considered statistically significant.

Results

Treatment Effect on 1st TUBO Tumor Implantation

The combinational therapy of Anti-neu and CpG-6 was assessed on TUBO breast cancer model (FIG. 6). Four treatment groups were formed on day 11 following s.c. inoculation of TUBO cells on the right flank of mice, when their tumor volume reaching 60-120 mm$^3$. Anti-neu was administrated i.v. weekly×3 week; while CpG-6 or its GC control given i.t. every three days×4 times. So the entire treatments were completed by day 24 since the 1st inoculation.

Similar body weights were observed in each four groups over the course of 48 day study period, suggesting well-tolerated treatments (FIG. 6A). As mice in vehicle group developed solid tumors with increasing size over time, intravenous injection of Anti-neu resulted in a significant suppression of tumor growth (p<0.0001 vs. PBS). Whereas no additional effect was revealed when co-treating with intratumoral GC control (FIG. 6B), combinational treatment with CpG-6 led to a further significant inhibition of tumor growth (p=0.0009 vs. GC control).

Tumor-bearing mice were sacrificed when their tumors surpassed the size of 3000 mm$^3$, and the survival rates (%) in each treatment groups were analyzed (FIG. 6C). All six mice were dead of large tumor in vehicle group by 40 days post TUBO cell inoculation; whereas only 1/3 tumor-bearing mice were sacrificed in Anti-neu treated group (p=0.006). Except one death due to technical accident, combinational treatment with CpG-6, but not its GC control, protected all mice from tumor-causing death (p=0.039 vs. Anti-neu±GC control).

TABLE 12

P values between each group on tumor growth
(Tukey's multiple comparisons test)

| Groups | Anti-neu + GC-ctrl | Anti-neu + PBS | Anti-neu + CpG-6 |
|---|---|---|---|
| PBS + PBS | <0.0001 | <0.0001 | <0.0001 |
| Anti-neu + CG-ctrl | — | 0.7854 | 0.0009 |
| Anti-neu + PBS | — | — | <0.0001 |

TABLE 13

P values between each group on survival
after 1$^{st}$ TUBO inoculation

| | PBS + PBS | Anti-neu + GC-ctrl | Anti-neu + PBS |
|---|---|---|---|
| Log-rank (Mantel-Cox) test | | | |
| Anti-neu + GC-ctrl | 0.0013 | — | — |
| Anti-neu + PBS | 0.006 | 0.9919 | — |
| Anti-neu + CpG-6 | <0.0001 | 0.0392 | 0.0392 |
| Gehan-Breslow-Wilcoxon test | | | |
| Anti-neu + GC-ctrl | 0.0023 | — | — |
| Anti-neu + PBS | 0.0072 | 0.9999 | — |
| Anti-neu + CpG-6 | <0.0001 | 0.0447 | 0.0447 |

Durable Effect of Treatment on 2$^{nd}$ TUBO Tumor Implantation

To evaluate any lasting treatment effect on new tumor formation, all survived mice in Anti-neu+CpG-6-treated group by day 50 were divided into two groups for re-challenge s.c. with either TUBO or 4T1 tumor cells on their left flanks. A set of naïve mice was also used as the control for TUBO or 4T1 tumor growth upon 1st inoculation. Body weight, tumor growth and survival data are shown in FIG. 7.

While no difference in body weight change was shown among four groups of mice (FIG. 7A); a significant reduction of tumor size was revealed in Anti-neu+CpG-6 recipients than the naïve mice after re/challenge with either corresponding TUBO (p<0.0001) or 4T1 (p=0.005) tumor cells (FIG. 7B). Although no major difference was found in two types of tumor growth in naïve mice; Anti-neu+CpG-6 recipients rejected the 2nd TUBO challenge (11/12 mice, 91.7%) more significantly (p=0.021) than the 1st 4T1 tumor implantation (6/11 mice, 54.5%). Furthermore, comparing with naïve mice who were all dead of tumor inoculation within 65 days (FIG. 7C), Anti-neu+HP07T06-recipients resulted in a significant protection from left flank-challenge with 2nd TUBO inoculation (p<0.0001), but not with the 1st 4T1 inoculation (p=0.056). The survival difference between the latter two groups is also statistically significant (p=0.009).

TABLE 14 p values between related groups on tumor
growth (Mann-Whitney unpaired t test)

| Groups | 4T1 ctrl | TUBO | TUBO ctrl |
|---|---|---|---|
| 4T1 | 0.0052 | 0.021 | — |
| 4T1 ctrl | — | — | 0.0825 |
| TUBO | — | — | <0.0001 |

TABLE 15

P values between related groups on survival after 2$^{nd}$ inoculation

| Prism test | 4T1 vs. 4T1 ctrl | TUBO vs. TUBO ctrl | 4T1 vs. TUBO | 4T1 ctrl vs. TUBO ctrl |
|---|---|---|---|---|
| Log-rank (Mantel-Cox) | 0.056 | <0.0001 | 0.0094 | 0.2971 |
| Gehan-Breslow-Wilcoxon | 0.0612 | 0.0002 | 0.0099 | 0.6198 |

Long Memory Effect of Combinational Treatment on 3$^{rd}$ TUBO Tumor Inoculation To expand the treatment study on immune memory formation, all survived mice in Anti-neu+CpG-6-treated subgroups by day 70 post 2$^{nd}$ TUBO inoculation, i.e. day 120 since 1$^{st}$ TUBO inoculation, were once again challenge s.c. with either the 3$^{rd}$ TUBO or 2$^{nd}$ 4 T1 tumor cells on their left flanks. A set of naïve mice was also used as the control for TUBO or 4T1 tumor growth upon their 1$^{st}$ inoculation. Body weight, tumor growth and survival data are all shown in FIG. 8.

While no difference in body weight change was exhibited among four groups of mice (FIG. 8A); a significant reduction of both tumor size was revealed in Anti-neu+CpG-6 recipients as compared with the naïve mice after challenge with TUBO (p<0.0001) or 4T1 (p=0.006) tumor cells (FIG. 8B). Although no major difference was found in two types of tumor growth in naïve mice; Anti-neu+CpG-6 recipients rejected the 3$^{rd}$ TUBO tumor more significantly (p<0.0001) than the 2$^{nd}$ 4 T1 implantation. Furthermore, comparing with naïve mice who were all dead of either tumor inoculation within 45 days (FIG. 8C), Anti-neu+CpG-6-recipients resulted in a significant protection (p=0.0003) from lower right flank-challenge with the 3$^{rd}$ TUBO (83%) than the 2$^{nd}$ 4 T1 (0%) within 60 days' inoculation.

TABLE 16

| Group | P values between related groups (Tukey's multiple comparisons test) | | |
|---|---|---|---|
| | 4T1 ctrl | TUBO | TUBO ctrl |
| 4T1 | 0.006 | <0.0001 | — |
| 4T1 ctrl | — | — | 0.9693 |
| TUBO | — | — | <0.0001 |

TABLE 17

| | P values between related groups on survival after 3$^{rd}$ inoculation | | | |
|---|---|---|---|---|
| Prism test | 4T1 vs 4T1 ctrl | TUBO vs TUBO ctrl | 4T1 vs TUBO | 4T1 ctrl vs TUBO ctrl |
| Log-rank (Mantel-Cox) | 0.0017 | 0.0001 | 0.0003 | 0.3107 |
| Gehan-Breslow-Wilcoxon | 0.0021 | 0.0001 | 0.0011 | 0.3463 |

The invention claimed is:

1. An immunomodulatory polynucleotide, comprising a sequence selected from the group consisting of: SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, and SEQ ID NO.: 12.

2. The immunomodulatory polynucleotide of claim 1, wherein said polynucleotide comprises a chemical modification.

3. The immunomodulatory polynucleotide of claim 1, wherein said polynucleotide comprises a modification of one or more phosphate groups.

4. The immunomodulatory polynucleotide of claim 3, wherein said modification of one or more phosphate groups is a phosphorothioate linkage.

5. The immunomodulatory polynucleotide of claim 3, wherein phosphate backbone of said polynucleotide is completely phosphorothioate-modified.

6. The immunomodulatory polynucleotide of claim 3, wherein the modification of one or more phosphate group is a linkage.

7. A method of modulating an immune response in a subject, comprising: administering to a subject an immunomodulatory polynucleotide selected from the group consisting of: SEQ ID NO.: 3, SEQ ID NO.: 4, SEQ ID NO.: 5, SEQ ID NO.: 6, and SEQ ID NO.: 11, in an amount sufficient to modulate an immune response in said individual.

8. A therapeutic combination, comprising:
(i) an effective amount of a targeted therapeutic against a cancer; and
(ii) an effective amount of an immunomodulatory polynucleotide according to claim 1, or a combination thereof.

9. The combination of claim 8, wherein said targeted therapeutic is capable of binding to a tumor cell specifically or preferably in comparison to a non-tumor cell.

10. The combination of claim 9, wherein said tumor cell is of a carcinoma, a sarcoma, a lymphoma, a myeloma, or a central nervous system cancer.

11. The combination of claim 8, wherein said targeted therapeutic is capable of binding to a tumor antigen specifically or preferably in comparison to a non-tumor antigen.

12. The combination of claim 11, wherein said tumor antigen is selected from the group consisting of: CD2, CD19, CD20, CD22, CD27, CD33, CD37, CD38, CD40, CD44, CD47, CD52, CD56, CD70, CD79, and CD137.

13. The combination of claim 11, wherein said tumor antigen is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING (stimulator of IFN genes), Syndecan-1, TACI, TAG-72, Tenascin, TIM3, TRAILR1, TRAILR2, VEGFR-1, VEGFR-2, VEGFR-3, and variants thereof.

14. The combination of claim 8, wherein said targeted therapeutic comprises an immunoglobulin, a protein, a peptide, a small molecule, a nanoparticle, or a nucleic acid.

15. The combination of claim 8, wherein said targeted therapeutic comprises an antibody, or a functional fragment thereof.

16. The combination of claim 15, wherein said antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Opdivo (nivolumab), Dacetuzumab, Urelumab, Tecentriq (atezolizumab, MPDL3280A), Lambrolizumab, Blinatumomab, CT-011, Keytruda (pembrolizumab, MK-3475), BMS-936559, MED14736, MSB0010718C, Imfinzi (durvalumab), Bavencio (avelumab) and margetuximab (MGAH22).

17. The combination of claim 14, wherein said targeted therapeutic comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

18. The combination of claim 8, further comprises a chemotherapeutic agent.

19. The combination of claim 18, wherein said chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

20. A method for treating a disease condition in a subject that is in need of such treatment, comprising: administering to the subject a composition comprising the immunomodulatory polynucleotide selected from the group consisting of: SEQ ID NO.: 3, SEQ ID NO.: 4, SEQ ID NO.: 5, SEQ ID NO.: 6, and SEQ ID NO.: 11, wherein the disease condition is colorectal cancer, melanoma, or breast cancer.

21. The method of claim 20, wherein polynucleotide is SEQ ID NO: 6.

22. The method of claim 20, wherein the polynucleotide comprises a chemical modification.

23. The method of claim 20, wherein the polynucleotide comprises a modification of one or more phosphate groups.

24. The method of claim 23, wherein the modification of one or more phosphate groups is a phosphorothioate linkage.

25. The method of claim 23, wherein the phosphate backbone of the polynucleotide is completely phosphorothioate-modified.

26. The method of claim 20, wherein the composition further comprises a targeted therapeutic against a cancer.

27. The method of claim 26, wherein the targeted therapeutic is capable of binding to a tumor cell specifically or preferably in comparison to a non-tumor cell.

28. The method of claim 27, wherein the tumor cell is of a carcinoma, a sarcoma, a lymphoma, a myeloma, or a central nervous system cancer.

29. The method of claim 26, wherein the targeted therapeutic is capable of binding to a tumor antigen specifically or preferably in comparison to a non-tumor antigen.

30. The method of claim 29, wherein the tumor antigen is selected from the group consisting of CD2, CD19, CD20, CD22, CD27, CD33, CD37, CD38, CD40, CD44, CD47, CD52, CD56, CD70, CD79, and CD137.

31. The method of claim 29, wherein the tumor antigen is selected from the group consisting of 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, STING (stimulator of IFN genes), Syndecan-1, TACI, TAG-72, Tenascin, TIM3, TRAILR1, TRAILR2, VEGFR-1, VEGFR-2, VEGFR-3, and variants thereof.

32. The method of claim 26, wherein the targeted therapeutic comprises an immunoglobulin, a protein, a peptide, a small molecule, a nanoparticle, or a nucleic acid.

33. The method of claim 26, wherein the targeted therapeutic comprises an antibody, or a functional fragment thereof.

34. The method of claim 33, wherein said antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Opdivo (nivolumab), Dacetuzumab, Urelumab, Tecentriq (atezolizumab, MPDL3280A), Lambrolizumab, Blinatumomab, CT-011, Keytruda (pembrolizumab, MK-3475), BMS-936559, MED14736, MSB0010718C, Imfinzi (durvalumab), Bavencio (avelumab) and margetuximab (MGAH22).

35. The method of claim 32, wherein said targeted therapeutic comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

36. The method of claim 26, wherein the composition further comprises a chemotherapeutic agent.

37. The method of claim 36, wherein the chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

* * * * *

SEQUENCE LISTING

```
<160> NUMBER OF SEQ ID NOS: 18

<210> SEQ ID NO 1
<211> LENGTH: 29
<212> TYPE: DNA
<213> ORGANISM: Artificial Sequence
<220> FEATURE:
<223> OTHER INFORMATION: CpG 1

<400> SEQUENCE: 1
tcgggaacgt tccccgcgtt cgaacgcgg                                      29

<210> SEQ ID NO 2
<211> LENGTH: 29
<212> TYPE: DNA
<213> ORGANISM: Artificial Sequence
<220> FEATURE:
<223> OTHER INFORMATION: CpG 2

<400> SEQUENCE: 2
tcgcgaacgt tcgcggcgtt cgaacgccg                                      29

<210> SEQ ID NO 3
<211> LENGTH: 29
<212> TYPE: DNA
<213> ORGANISM: Artificial Sequence
<220> FEATURE:
<223> OTHER INFORMATION: CpG 3

<400> SEQUENCE: 3
tcgcgaacgt tcgccgggtt cgaacccgg                                      29

<210> SEQ ID NO 4
<211> LENGTH: 29
<212> TYPE: DNA
<213> ORGANISM: Artificial Sequence
<220> FEATURE:
<223> OTHER INFORMATION: CpG 4

<400> SEQUENCE: 4
tcgcgaacgt tcgccgcctt cgaaggcgg                                      29

<210> SEQ ID NO 5
<211> LENGTH: 29
<212> TYPE: DNA
<213> ORGANISM: Artificial Sequence
<220> FEATURE:
<223> OTHER INFORMATION: CpG 5

<400> SEQUENCE: 5
tcgcgaacgt tcgccgcgat cgatcgcgg                                      29

<210> SEQ ID NO 6
```

```
<211> LENGTH: 29
<212> TYPE: DNA
<213> ORGANISM: Artificial Sequence
<220> FEATURE:
<223> OTHER INFORMATION: CpG 6

<400> SEQUENCE: 6
tcgcgaacgt tcgccgcgta cgtacgcgg                                        29

<210> SEQ ID NO 7
<211> LENGTH: 30
<212> TYPE: DNA
<213> ORGANISM: Artificial Sequence
<220> FEATURE:
<223> OTHER INFORMATION: CpG 7

<400> SEQUENCE: 7
tcgcgaacgt tcgcgcgcgt tcgaacgcgg                                       30

<210> SEQ ID NO 8
<211> LENGTH: 33
<212> TYPE: DNA
<213> ORGANISM: Artificial Sequence
<220> FEATURE:
<223> OTHER INFORMATION: CpG 8

<400> SEQUENCE: 8
tcgccgaacg ttcggccgcg gttcgaaccg cgg                                   33

<210> SEQ ID NO 9
<211> LENGTH: 30
<212> TYPE: DNA
<213> ORGANISM: Artificial Sequence
<220> FEATURE:
<223> OTHER INFORMATION: CpG 9

<400> SEQUENCE: 9
tcgcgaacgt tcgctcgcgt tcgaacgcgg                                       30

<210> SEQ ID NO 10
<211> LENGTH: 31
<212> TYPE: DNA
<213> ORGANISM: Artificial Sequence
<220> FEATURE:
<223> OTHER INFORMATION: CpG 10

<400> SEQUENCE: 10
tcgcgaacgt tcgccgacgt tcgaacgtcg g                                     31

<210> SEQ ID NO 11
<211> LENGTH: 27
<212> TYPE: DNA
<213> ORGANISM: Artificial Sequence
<220> FEATURE:
<223> OTHER INFORMATION: CpG 11

<400> SEQUENCE: 11
tcgcgaacgt tcgccggttc gaaccgg                                          27

<210> SEQ ID NO 12
<211> LENGTH: 27
<212> TYPE: DNA
<213> ORGANISM: Artificial Sequence
<220> FEATURE:
<223> OTHER INFORMATION: CpG 12

<400> SEQUENCE: 12
```

```
tcgcgaacgt tcgccgcttc gaagcgg                                        27
```

<210> SEQ ID NO 13
<211> LENGTH: 20
<212> TYPE: DNA
<213> ORGANISM: Artificial Sequence
<220> FEATURE:
<223> OTHER INFORMATION: A type CpG2216

<400> SEQUENCE: 13

```
ggggqacgat cgtcggqgqg                                                20
```

<210> SEQ ID NO 14
<211> LENGTH: 24
<212> TYPE: DNA
<213> ORGANISM: Artificial Sequence
<220> FEATURE:
<223> OTHER INFORMATION: B type CpG2006

<400> SEQUENCE: 14

```
tcgtcgtttt gtcgttttgt cgtt                                           24
```

<210> SEQ ID NO 15
<211> LENGTH: 23
<212> TYPE: DNA
<213> ORGANISM: Artificial Sequence
<220> FEATURE:
<223> OTHER INFORMATION: B type CpG684

<400> SEQUENCE: 15

```
tcgacgttcg tcgttcgtcg ttc                                            23
```

<210> SEQ ID NO 16
<211> LENGTH: 22
<212> TYPE: DNA
<213> ORGANISM: Artificial Sequence
<220> FEATURE:
<223> OTHER INFORMATION: B type CpG1018

<400> SEQUENCE: 16

```
tgactgtgaa cgttcgagat ga                                             22
```

<210> SEQ ID NO 17
<211> LENGTH: 22
<212> TYPE: DNA
<213> ORGANISM: Artificial Sequence
<220> FEATURE:
<223> OTHER INFORMATION: C type CpG2395

<400> SEQUENCE: 17

```
tcgtcgtttt cggcgcgcgc cg                                             22
```

<210> SEQ ID NO 18
<211> LENGTH: 29
<212> TYPE: DNA
<213> ORGANISM: Artificial Sequence
<220> FEATURE:
<223> OTHER INFORMATION: GC-ODN

<400> SEQUENCE: 18

```
tggccaagct tgggcccctt gcaagggcc                                      29
```